United States Patent
Wang et al.

(10) Patent No.: US 11,369,280 B2
(45) Date of Patent: Jun. 28, 2022

(54) VELOCITY-MATCHED ULTRASONIC TAGGING IN PHOTOACOUSTIC FLOWGRAPHY

(71) Applicant: California Institute of Technology, Pasadena, CA (US)

(72) Inventors: Lihong Wang, Arcadia, CA (US); Xiaoming Wei, Guangzhou (CN)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 253 days.

(21) Appl. No.: 16/806,796

(22) Filed: Mar. 2, 2020

(65) Prior Publication Data
US 2020/0275846 A1 Sep. 3, 2020

Related U.S. Application Data

(60) Provisional application No. 62/812,426, filed on Mar. 1, 2019.

(51) Int. Cl.
*A61B 5/0285* (2006.01)
*A61B 5/00* (2006.01)
*A61B 90/92* (2016.01)

(52) U.S. Cl.
CPC .......... *A61B 5/0285* (2013.01); *A61B 5/0051* (2013.01); *A61B 5/0095* (2013.01); *A61B 5/418* (2013.01); *A61B 90/92* (2016.02)

(58) Field of Classification Search
None
See application file for complete search history.

(56) References Cited

U.S. PATENT DOCUMENTS

| | | | |
|---|---|---|---|
| 4,029,756 A | 6/1977 | Gaafar | |
| 4,127,318 A | 11/1978 | Determann et al. | |
| 4,255,971 A | 3/1981 | Rosencwaig | |
| 4,267,732 A | 5/1981 | Quate | |
| 4,284,324 A | 8/1981 | Huignard et al. | |
| 4,375,818 A | 3/1983 | Suwaki et al. | |
| 4,385,634 A | 5/1983 | Bowen | |
| 4,430,897 A | 2/1984 | Quate | |
| 4,430,987 A | 2/1984 | Heller | |
| 4,462,255 A | 7/1984 | Guess et al. | |
| 4,468,136 A | 8/1984 | Murphy et al. | |
| 4,489,727 A | 12/1984 | Matsuo et al. | |
| 4,546,771 A | 10/1985 | Eggleton et al. | |

(Continued)

FOREIGN PATENT DOCUMENTS

CN 1883379 A 12/2006
EP 0012262 A1 6/1980

(Continued)

OTHER PUBLICATIONS

Office Action from related U.S. Appl. No. 11/625,099, dated Nov. 1, 2010.

(Continued)

*Primary Examiner* — Amelie R Davis
*Assistant Examiner* — Marjan Saboktakin
(74) *Attorney, Agent, or Firm* — Sheila Martinez-Lemke; Weaver Austin Villeneuve & Sampson LLP

(57) ABSTRACT

Among the various aspects of the present disclosure is the provision of systems and methods of velocity-matched ultrasonic tagging in photoacoustic flowgraphy.

24 Claims, 9 Drawing Sheets

(56) References Cited

U.S. PATENT DOCUMENTS

| | | |
|---|---|---|
| 4,596,254 A | 6/1986 | Adrian et al. |
| 4,687,304 A | 8/1987 | Piller et al. |
| 4,740,081 A | 4/1988 | Martens et al. |
| 4,802,461 A | 2/1989 | Cho |
| 4,802,487 A | 2/1989 | Martin et al. |
| 4,809,703 A | 3/1989 | Ishikawa et al. |
| 4,850,363 A | 7/1989 | Yanagawa |
| 4,860,758 A | 8/1989 | Yanagawa et al. |
| 4,869,256 A | 9/1989 | Kanno et al. |
| 4,872,758 A | 10/1989 | Miyazaki et al. |
| 4,921,333 A | 5/1990 | Brody et al. |
| 4,929,951 A | 5/1990 | Small |
| 4,995,396 A | 2/1991 | Inaba et al. |
| 5,070,455 A | 12/1991 | Singer et al. |
| 5,083,549 A | 1/1992 | Cho et al. |
| 5,107,844 A | 4/1992 | Kami et al. |
| 5,115,814 A | 5/1992 | Griffith et al. |
| 5,125,410 A | 6/1992 | Misono et al. |
| 5,140,463 A | 8/1992 | Yoo et al. |
| 5,170,793 A | 12/1992 | Takano et al. |
| 5,194,723 A | 3/1993 | Cates et al. |
| 5,207,672 A | 5/1993 | Roth et al. |
| 5,227,912 A | 7/1993 | Ho et al. |
| 5,305,759 A | 4/1994 | Kaneko et al. |
| 5,321,501 A | 6/1994 | Swanson et al. |
| 5,329,817 A | 7/1994 | Garlick et al. |
| 5,331,466 A | 7/1994 | Van Saarloos |
| 5,345,938 A | 9/1994 | Nishiki et al. |
| 5,373,845 A | 12/1994 | Gardineer et al. |
| 5,414,623 A | 5/1995 | Lu et al. |
| 5,445,155 A | 8/1995 | Sieben |
| 5,465,722 A | 11/1995 | Fort et al. |
| 5,546,187 A | 8/1996 | Pepper et al. |
| 5,546,947 A | 8/1996 | Yagami et al. |
| 5,546,948 A | 8/1996 | Hamm et al. |
| 5,606,975 A | 3/1997 | Liang et al. |
| 5,615,675 A | 4/1997 | O'Donnell et al. |
| 5,635,784 A | 6/1997 | Seale |
| 5,651,366 A | 7/1997 | Liang et al. |
| 5,713,356 A | 2/1998 | Kruger |
| 5,718,231 A | 2/1998 | Dewhurst et al. |
| 5,781,294 A | 7/1998 | Nakato et al. |
| 5,836,872 A | 11/1998 | Kenet et al. |
| 5,840,023 A | 11/1998 | Oraevsky et al. |
| 5,860,934 A | 1/1999 | Sarvazyan |
| 5,913,234 A | 6/1999 | Julliard et al. |
| 5,971,998 A | 10/1999 | Russell et al. |
| 5,977,538 A | 11/1999 | Unger et al. |
| 5,991,697 A | 11/1999 | Nelson et al. |
| 6,055,097 A | 4/2000 | Lanni et al. |
| 6,102,857 A | 8/2000 | Kruger |
| 6,104,942 A | 8/2000 | Kruger |
| 6,108,576 A | 8/2000 | Alfano et al. |
| 6,111,645 A | 8/2000 | Tearney et al. |
| 6,134,003 A | 10/2000 | Tearney et al. |
| 6,216,025 B1 | 4/2001 | Kruger |
| 6,233,055 B1 | 5/2001 | Mandella et al. |
| 6,282,011 B1 | 8/2001 | Tearney et al. |
| 6,292,682 B1 | 9/2001 | Kruger |
| 6,309,352 B1 | 10/2001 | Oraevsky et al. |
| 6,341,036 B1 | 1/2002 | Tearney et al. |
| 6,379,325 B1 | 4/2002 | William et al. |
| 6,405,069 B1 | 6/2002 | Oraevsky et al. |
| 6,413,228 B1 | 7/2002 | Hung et al. |
| 6,421,164 B2 | 7/2002 | Tearney et al. |
| 6,432,067 B1 | 8/2002 | Martin et al. |
| 6,466,806 B1 | 10/2002 | Geva et al. |
| 6,485,413 B1 | 11/2002 | Boppart et al. |
| 6,490,470 B1 | 12/2002 | Kruger |
| 6,498,942 B1 | 12/2002 | Esenaliev et al. |
| 6,498,945 B1 | 12/2002 | Alfheim et al. |
| 6,501,551 B1 | 12/2002 | Tearney et al. |
| 6,545,264 B1 | 4/2003 | Stern |
| 6,564,087 B1 | 5/2003 | Pitris et al. |
| 6,567,688 B1 | 5/2003 | Wang |
| 6,590,830 B1 | 7/2003 | Garlick et al. |
| 6,626,834 B2 | 9/2003 | Dunnie et al. |
| 6,628,404 B1 | 9/2003 | Kelley et al. |
| 6,633,774 B2 | 10/2003 | Kruger |
| 6,654,630 B2 | 11/2003 | Zuluaga et al. |
| 6,658,279 B2 | 12/2003 | Swanson et al. |
| 6,694,173 B1 | 2/2004 | Bende et al. |
| 6,701,181 B2 | 3/2004 | Tang et al. |
| 6,751,490 B2 | 6/2004 | Esenaliev et al. |
| 6,764,450 B2 | 7/2004 | Yock |
| 6,831,781 B2 | 12/2004 | Tearney et al. |
| 6,833,540 B2 | 12/2004 | MacKenzie et al. |
| 6,839,496 B1 | 1/2005 | Mills et al. |
| 6,846,288 B2 | 1/2005 | Nagar et al. |
| 6,853,446 B1 | 2/2005 | Almogy et al. |
| 6,877,894 B2 | 4/2005 | Vona et al. |
| 6,937,886 B2 | 8/2005 | Zavislan |
| 6,956,650 B2 | 10/2005 | Boas et al. |
| 7,072,045 B2 | 7/2006 | Chen et al. |
| 7,198,778 B2 | 4/2007 | Achilefu et al. |
| 7,231,243 B2 | 6/2007 | Tearney et al. |
| 7,245,789 B2 | 7/2007 | Bates et al. |
| 7,266,407 B2 | 9/2007 | Li et al. |
| 7,322,972 B2 | 1/2008 | Viator et al. |
| 7,357,029 B2 | 4/2008 | Falk |
| 7,382,949 B2 | 6/2008 | Bouma et al. |
| 7,541,602 B2 | 6/2009 | Metzger et al. |
| 7,610,080 B1 | 10/2009 | Winchester, Jr. et al. |
| 7,917,312 B2 | 3/2011 | Wang et al. |
| 8,016,419 B2 | 9/2011 | Zhang et al. |
| 8,025,406 B2 | 9/2011 | Zhang et al. |
| 8,143,605 B2 | 3/2012 | Metzger et al. |
| 8,397,573 B2 | 3/2013 | Kobayashi |
| 8,416,421 B2 | 4/2013 | Wang et al. |
| 8,454,512 B2 | 6/2013 | Wang et al. |
| 8,891,088 B2 | 11/2014 | Goldschmidt et al. |
| 8,997,572 B2 | 4/2015 | Wang et al. |
| 9,220,415 B2 | 12/2015 | Mandelis et al. |
| 9,234,841 B2 | 1/2016 | Wang et al. |
| 9,335,605 B2 | 5/2016 | Wang et al. |
| 9,528,966 B2 | 12/2016 | Wang et al. |
| 9,618,445 B2 | 4/2017 | Sun et al. |
| 10,359,400 B2 | 7/2019 | Wang et al. |
| 10,433,733 B2 | 10/2019 | Wang et al. |
| 10,448,850 B2 | 10/2019 | Wang et al. |
| 2001/0052979 A1 | 12/2001 | Treado et al. |
| 2002/0093637 A1 | 7/2002 | Yuan et al. |
| 2002/0173780 A1 | 11/2002 | Altshuler et al. |
| 2002/0176092 A1 | 11/2002 | Deck |
| 2003/0097066 A1 | 5/2003 | Shelby et al. |
| 2003/0160957 A1 | 8/2003 | Oldham et al. |
| 2003/0160967 A1 | 8/2003 | Houston et al. |
| 2004/0030255 A1 | 2/2004 | Alfano et al. |
| 2004/0039379 A1 | 2/2004 | Viator et al. |
| 2004/0082070 A1 | 4/2004 | Jones et al. |
| 2004/0254474 A1 | 12/2004 | Seibel et al. |
| 2005/0015002 A1 | 1/2005 | Dixon et al. |
| 2005/0028482 A1 | 2/2005 | Cable et al. |
| 2005/0143664 A1 | 6/2005 | Chen et al. |
| 2005/0154313 A1 | 7/2005 | Desilets et al. |
| 2005/0168749 A1 | 8/2005 | Ye et al. |
| 2005/0217381 A1 | 10/2005 | Falk |
| 2005/0234315 A1 | 10/2005 | Mayevsky et al. |
| 2005/0277824 A1 | 12/2005 | Aubry et al. |
| 2006/0055936 A1 | 3/2006 | Yun et al. |
| 2006/0058614 A1 | 3/2006 | Tsujita |
| 2006/0122516 A1 | 6/2006 | Schmidt et al. |
| 2006/0181791 A1 | 8/2006 | Van Beek et al. |
| 2006/0184042 A1 | 8/2006 | Wang et al. |
| 2006/0235299 A1 | 10/2006 | Martinelli |
| 2006/0247510 A1 | 11/2006 | Wiemker et al. |
| 2006/0264717 A1 | 11/2006 | Pesach et al. |
| 2007/0088206 A1 | 4/2007 | Peyman et al. |
| 2007/0093702 A1* | 4/2007 | Yu ............ A61B 5/0051 600/326 |
| 2007/0213590 A1 | 9/2007 | Squicciarini |
| 2007/0213618 A1 | 9/2007 | Li et al. |
| 2007/0213693 A1 | 9/2007 | Plunkett |
| 2007/0282200 A1 | 12/2007 | Johnson et al. |

(56) References Cited

U.S. PATENT DOCUMENTS

| | | |
|---|---|---|
| 2007/0299341 A1 | 12/2007 | Wang et al. |
| 2008/0029711 A1 | 2/2008 | Viellerobe et al. |
| 2008/0037367 A1 | 2/2008 | Gross et al. |
| 2008/0088838 A1 | 4/2008 | Raicu et al. |
| 2008/0123083 A1 | 5/2008 | Wang et al. |
| 2008/0173093 A1 | 7/2008 | Wang et al. |
| 2008/0230717 A1 | 9/2008 | Ashkenazi et al. |
| 2009/0051900 A1 | 2/2009 | Moon et al. |
| 2009/0054763 A1 | 2/2009 | Wang et al. |
| 2009/0088631 A1 | 4/2009 | Dietz et al. |
| 2009/0116518 A1 | 5/2009 | Patel et al. |
| 2009/0138215 A1 | 5/2009 | Wang et al. |
| 2009/0185191 A1 | 7/2009 | Boppart et al. |
| 2009/0227997 A1 | 9/2009 | Wang et al. |
| 2010/0079768 A1 | 4/2010 | Wang et al. |
| 2010/0134793 A1 | 6/2010 | Krishnamachari et al. |
| 2010/0245766 A1 | 9/2010 | Zhang et al. |
| 2010/0245769 A1 | 9/2010 | Zhang et al. |
| 2010/0245770 A1 | 9/2010 | Zhang et al. |
| 2010/0249562 A1 | 9/2010 | Zhang et al. |
| 2010/0268042 A1 | 10/2010 | Wang et al. |
| 2010/0285518 A1 | 11/2010 | Viator et al. |
| 2010/0309466 A1 | 12/2010 | Lucassen et al. |
| 2010/0322497 A1 | 12/2010 | Dempsey et al. |
| 2011/0071402 A1 | 3/2011 | Masumura |
| 2011/0122416 A1 | 5/2011 | Yang et al. |
| 2011/0201914 A1 | 8/2011 | Wang et al. |
| 2011/0251515 A1 | 10/2011 | Leuthardt et al. |
| 2011/0275890 A1 | 11/2011 | Wang et al. |
| 2011/0282181 A1 | 11/2011 | Wang et al. |
| 2011/0282192 A1 | 11/2011 | Axelrod et al. |
| 2012/0065490 A1* | 3/2012 | Zharov .......... A61B 5/416 600/407 |
| 2012/0070817 A1 | 3/2012 | Wang et al. |
| 2012/0074294 A1 | 3/2012 | Streuber et al. |
| 2012/0118052 A1 | 5/2012 | O'Donnell et al. |
| 2012/0204648 A1 | 8/2012 | Wang et al. |
| 2012/0275262 A1 | 11/2012 | Song et al. |
| 2012/0307250 A1 | 12/2012 | Wang |
| 2013/0151188 A1* | 6/2013 | Rokni .......... A61B 5/0097 702/100 |
| 2013/0199299 A1 | 8/2013 | Wang et al. |
| 2013/0218002 A1 | 8/2013 | Kiraly |
| 2013/0245406 A1 | 9/2013 | Wang et al. |
| 2014/0009808 A1 | 1/2014 | Wang et al. |
| 2014/0142404 A1 | 5/2014 | Wang et al. |
| 2014/0356897 A1 | 12/2014 | Wang et al. |
| 2015/0005613 A1 | 1/2015 | Kim et al. |
| 2015/0185187 A1 | 7/2015 | Wang et al. |
| 2015/0245771 A1 | 9/2015 | Wang et al. |
| 2015/0272444 A1 | 10/2015 | Maslov et al. |
| 2015/0272446 A1 | 10/2015 | Wang et al. |
| 2015/0316510 A1 | 11/2015 | Fukushima et al. |
| 2016/0081558 A1 | 3/2016 | Wang et al. |
| 2016/0235305 A1 | 8/2016 | Wang et al. |
| 2016/0242651 A1 | 8/2016 | Wang et al. |
| 2016/0249812 A1 | 9/2016 | Wang et al. |
| 2016/0262628 A1 | 9/2016 | Wang et al. |
| 2016/0305914 A1 | 10/2016 | Wang et al. |
| 2016/0310083 A1 | 10/2016 | Wang et al. |
| 2016/0345886 A1 | 12/2016 | Wang et al. |
| 2017/0065182 A1 | 3/2017 | Wang et al. |
| 2017/0105636 A1 | 4/2017 | Wang et al. |
| 2017/0367586 A9 | 12/2017 | Wang et al. |
| 2018/0020920 A1 | 1/2018 | Ermilov et al. |
| 2018/0132728 A1 | 5/2018 | Wang et al. |
| 2019/0008444 A1 | 1/2019 | Wang et al. |
| 2019/0125583 A1 | 5/2019 | Wang et al. |
| 2019/0227038 A1 | 7/2019 | Wang et al. |
| 2019/0307334 A1 | 10/2019 | Wang et al. |
| 2020/0056986 A1 | 2/2020 | Wang et al. |
| 2020/0073103 A1 | 3/2020 | Wang et al. |
| 2020/0268253 A1 | 8/2020 | Wang et al. |
| 2020/0397523 A1 | 12/2020 | Gao et al. |
| 2021/0010976 A1 | 1/2021 | Wang et al. |

FOREIGN PATENT DOCUMENTS

| | | |
|---|---|---|
| EP | 0919180 A1 | 6/1999 |
| EP | 1493380 A1 | 1/2005 |
| JP | 05-126725 A | 5/1993 |
| JP | 2000/292416 A | 10/2000 |
| JP | 2009/068977 A | 4/2009 |
| JP | 2010/017426 A | 1/2010 |
| JP | 2010/040161 A | 2/2010 |
| JP | 2012/143384 A | 8/2012 |
| JP | 2014124242 A | 7/2014 |
| JP | 2014/224806 A | 12/2014 |
| JP | 2016-101260 A | 6/2016 |
| JP | 6086718 B2 | 3/2017 |
| KR | 100946550 B1 | 3/2010 |
| KR | 2017-0006470 A | 1/2017 |
| WO | WO2006/111929 A1 | 10/2006 |
| WO | WO2007/088709 A1 | 8/2007 |
| WO | WO2007/148239 A2 | 12/2007 |
| WO | WO2008/062354 A1 | 5/2008 |
| WO | WO2008/100386 A2 | 8/2008 |
| WO | WO2009/055705 A2 | 4/2009 |
| WO | WO2010/048258 A1 | 4/2010 |
| WO | WO2010/080991 A2 | 7/2010 |
| WO | WO2011/060101 A2 | 5/2011 |
| WO | WO2011/091360 A2 | 7/2011 |
| WO | WO2011/127428 A2 | 10/2011 |
| WO | WO2012/035472 A1 | 3/2012 |
| WO | WO2013/086293 A1 | 6/2013 |
| WO | WO2015/118881 A1 | 8/2015 |
| WO | WO2018/102446 A2 | 6/2018 |
| WO | WO2018/209046 A1 | 11/2018 |

OTHER PUBLICATIONS

Final Office Action from related U.S. Appl. No. 11/625,099, dated Apr. 20, 2010.
Office Action from related U.S. Appl. No. 12/254,643, dated Aug. 6, 2010.
Notice of Allowance from related U.S. Appl. No. 12/254,643, dated Nov. 22, 2010.
Office Action from related U.S. Appl. No. 12/568,069, dated Dec. 21, 2012.
Office Action from related U.S. Appl. No. 12/568,069, dated Mar. 29, 2012.
Final Office Action from related U.S. Appl. No. 12/568,069, dated Sep. 18, 2012.
Notice of Allowance from related U.S. Appl. No. 12/568,069, dated Feb. 22, 2013.
Office Action from related U.S. Appl. No. 12/739,589, dated Jul. 19, 2012.
Notice of Allowance from related U.S. Appl. No. 12/739,589, dated Feb. 5, 2013.
Office Action from related U.S. Appl. No. 13/125,522, dated Jan. 22, 2013.
Final Office Action from related U.S. Appl. No. 13/125,522, dated May 23, 2013.
Office Action from related U.S. Appl. No. 13/125,522, dated Jul. 17, 2014.
Final Office Action from related U.S. Appl. No. 13/125,522, dated Oct. 29, 2014.
Office Action dated Aug. 26, 2015 issued in U.S. Appl. No. 13/125,522.
Final Office Action dated Mar. 3, 2016 issued in U.S. Appl. No. 13/125,522.
Notice of Allowance dated Sep. 19, 2016 issued in U.S. Appl. No. 13/125,522.
Office Action from related U.S. Appl. No. 13/143,832, dated Apr. 18, 2014.
Office Action from related U.S. Appl. No. 13/450,793, dated Jun. 5, 2013.
Final Office Action from related U.S. Appl. No. 13/450,793, dated Nov. 22, 2013.
Office Action from related U.S. Appl. No. 13/450,793, dated Mar. 24, 2014.

(56) References Cited

OTHER PUBLICATIONS

Office Action from related U.S. Appl. No. 13/450,793, dated Aug. 1, 2014.
Office Action from related U.S. Appl. No. 13/574,994, dated Mar. 17, 2014.
Final Office Action from related U.S. Appl. No. 13/574,994, dated Aug. 26, 2014.
Notice of Allowance dated Nov. 17, 2015 from U.S. Appl. No. 13/574,994.
Office Action dated Jan. 20, 2015, from U.S. Appl. No. 14/026,577.
Final Office Action dated Sep. 30, 2015, from U.S. Appl. No. 14/026,577.
Notice of Allowance dated Jan. 5, 2016, from U.S. Appl. No. 14/026,577.
Office Action dated Nov. 13, 2017, from U.S. Appl. No. 15/148,685.
Final Office Action dated Sep. 24, 2018, from U.S. Appl. No. 15/148,685.
Notice of Allowance dated May 16, 2019, from U.S. Appl. No. 15/148,685.
Office Action from related U.S. Appl. No. 13/637,897, dated Aug. 1, 2014.
Office Action from related U.S. Appl. No. 14/164,117, dated Dec. 11, 2015.
Office Action dated Dec. 13, 2019 issued in U.S. Appl. No. 15/037,468.
Notice of Allowance dated Mar. 23, 2020 issued in U.S. Appl. No. 15/037,468.
Notice of Allowance dated Oct. 28, 2020 issued in U.S. Appl. No. 15/037,468.
Office Action dated Oct. 3, 2018 issued in U.S. Appl. No. 14/436,581.
Amendment and Request for Continued Examination dated Nov. 25, 2019 in U.S. Appl. No. 14/436,581.
Final Office Action dated May 24, 2019 issued in U.S. Appl. No. 14/436,581.
Office Action dated Apr. 3, 2020 issued in U.S. Appl. No. 14/436,581.
Notice of Allowance dated Jan. 26, 2021 issued in U.S. Appl. No. 14/436,581.
Office Action dated Jun. 20, 2014 issued in U.S. Appl. No. 13/369,558.
Notice of Allowance dated Jul. 29, 2014 issued in U.S. Appl. No. 13/369,558.
Notice of Allowance dated Dec. 5, 2014 issued in U.S. Appl. No. 13/369,558.
Office Action dated Apr. 21, 2017 issued in U.S. Appl. No. 14/639,676.
Final Office Action dated Nov. 15, 2017 issued in U.S. Appl. No. 14/639,676.
Office Action dated May 31, 2018 issued in U.S. Appl. No. 14/639,676.
Notice of Allowance dated Dec. 12, 2018 issued in U.S. Appl. No. 14/639,676.
Office Action dated Feb. 28, 2020 issued in U.S. Appl. No. 16/372,597.
Office Action dated Aug. 19, 2019 issued in U.S. Appl. No. 16/372,597.
Office Action dated Oct. 8, 2020 issued in U.S. Appl. No. 16/372,597.
The International Search Report and Written Opinion dated Mar. 27, 2014 issued in Application No. PCT/US2013/065594.
The International Search Report and the Written Opinion of the International Searching Authority, or the Declaration, for PCT/US2009/061435, dated Mar. 29, 2010, 6 pages.
The International Search Report and the Written Opinion of the International Searching Authority, dated Sep. 22, 2011, from related application No. PCT/US2011/022253, 6 pgs.
International Search Report of International Application No. PCT/US2014/066437, dated Feb. 26, 2015, 3 pages.
Partial European Search Report issued for European Application No. 17159220.7, dated Aug. 23, 2017 (9 pages).
International Search Report and Written Opinion dated Apr. 22, 2009, from Application No. PCT/US2008/081167 (7 pages).
International Search Report and Written Opinion from Application Serial No. PCT/US2010/020488, dated Aug. 31, 2010 (10 pages).
International Search Report and Written Opinion from Application Serial No. PCT/US2011/031823, dated Dec. 26, 2011 (8 pages).
International Search Report and Written Opinion from Application Serial No. PCTIUS2012/068403, dated Mar. 19, 2013 (10 pages).
Extended European Search Report from European Application Serial No. 08842292.8, dated Dec. 17, 2013 (8 pages).
Final Office Action from related Japanese Patent Application No. JP 2010-531281, dated Mar. 11, 2014, (5 pages).
International Search Report and Written Opinion dated Dec. 2, 2019, issued in Application No. PCT/US2019/046574.
International Search Report and Written Opinion dated Dec. 23, 2019, issued in Application No. PCT/US2019/049594.
International Search Report and Written Opinion dated Aug. 31, 2020, issued in Application No. PCT/US2020/019368.
International Search Report and Written Opinion dated Oct. 14, 2020, issued in Application No. PCT/US2020/07174.
International Search Report dated Aug. 9, 2018 issued in Application No. PCT/US2018/032007.
Written Opinion of the International Searching Authority dated Aug. 9, 2018 issued in Application No. PCT/US2018/032007.
International Preliminary Report on Patentability dated Nov. 12, 2019 issued in PCT/US2018/032007.
Abdelmohsen, et al., "Micro- and nano-motors for biomedical applications," J. Mater. Chem. B 2, (2014) pp. 2395-2408.
Al, et al., "Spectral-domain optical coherence tomography: Removal of autocorrelation using an optical switch," Applied Physics Letters, (Mar. 15, 2006), 88(11): pp. 111115-1-111115-3. <doi:10.1063/1.2186520>.
Allen, et al. "Pulsed Near-Infrared Laser Diode Excitation System for Biomedical Photoacoustic Imaging," Optics Letters, Optical Society of America, USA., vol. 31, No. 23, Dec. 1, 2006, pp. 3462-3464.
Alomair, et al., "In vivo high angular resolution diffusion-weighted imaging of mouse brain at 16.4 Tesla," PloS One 10, Jun. 25, 2015, e0130133, pp. 1-17.
Arridge, et al., "Accelerated high-resolution photoacoustic tomography via compressed sensing," ArXiv Prepr. ArXiv160500133, 2016, pp. 8908-8940.
Aubry J.-F., et al., "Experimental demonstration of noninvasive transskull adaptive focusing based on prior computed tomography scans," J. Acoust. Soc. Am. 113(1), 84-93 (2003). (Year: 2003).
Baheiraei, et al., "Investigation of magnesium incorporation within gelatin/calcium phosphate nanocomposite scaffold for bone tissue engineering," Int. J. Appl. Ceram. Technol. 12, (2015) pp. 245-253.
Baker, M. J. et al., "Using Fourier transform IR spectroscopy to analyze biological materials," Nat. Protoc. 9, 1771-1791 (2014).
Bansil, et al., "The biology of mucus: Composition, synthesis and organization" Adv. Drug Deliv. Rev. 124, (2018) pp. 3-15.
Beaven, G. H. & Holiday, E. R., "Ultraviolet absorption spectra of proteins and amino acids," Adv. Protein Chem 7, 319-386 (1952).
Bell, A.G., "On the Production and Reproduction of Sound by Light," American Journal of Sciences, Oct. 1880, pp. 305-324, Third Series, vol. XX, USA.
Bellinger, et al., "Oral, ultra-long-lasting drug delivery: Application toward malaria elimination goals" Sci Transl. Med. 8(365), Nov. 16, 2016, 365ra157, pp. 1-25. <doi:10.1126/scitranslmed.aag2374>.
Bioucas-Dias, J.M. and Figueiredo, M.A.T. "A new TwIST: two-step iterative shrinkage/thresholding algorithms for image restoration," IEEE Trans. Image Process. 16, 2992-3004 (Dec. 2007).
Brenner, et al., "Computed Tomography—An Increasing Source of Radiation Exposure" N. Engl. J. Med 357;22, Nov. 29, 2007, pp. 2277-2284.
Calasso et al., "Photoacoustic Point Source," Physical Review Letters, vol. 86, No. 16, Apr. 16, 2001, pp. 3550-3553.
Cannata et al., "Development of a 35-MHz Piezo-Composite Ultrasound Array for Medical Imaging," IEE Transactions on Ultrasonics, Ferroelectrics, and Frequency Control, 53(1): pp. 224-236 (2006).
Celli, J. P., et al., "Helicobacter pylori moves through mucus by reducing mucin viscoelasticity," Proc. Natl. Acad. Sci. U. S. A. 106, (2009) pp. 14321-14326.

(56) References Cited

OTHER PUBLICATIONS

Chan, et al., "New opportunities in micro- and macro-attenuated total reflection infrared spectroscopic imaging: spatial resolution and sampling versatility," Appl. Spectrosc. 57, 381-389 (2003).

Cheng, J.-X. Et al., "Vibrational spectroscopic imaging ofliving systems: an emerging platform for biology and medicine," Science, vol. 350 aaa8870, No. 6264, Nov. 27, 2015, pp. 1054-1063.

Cheong, et al., "A review of the optical properties of biological tissues," IEEE J. Quantum Electronics, 26(12): pp. 2166-2185 (1980).

Chourasia, et al., "Design and Development of Multiparticulate System for Targeted Drug Delivery to Colon," Drug Delivery, 11:3, (2004) pp. 201-207.

Cox, B., Beard, P., "Photoacoustic tomography with a single detector in a reverberant cavity" J. Acoust. Soc. Am. 125, 1426 (Mar. 2009).

Cox, et al., "Artifact trapping during time reversal photoacoustic imaging for acoustically heterogeneous media," IEEE Trans. Med. Imaging, vol. 29, No. 2, (2010) pp. 387-396.

Cui, Y., et al. "Transferring-conjugated magnetic silica PLGA nanoparticles loaded with doxorubicin and paclitaxel for brain glioma treatment," Biomaterials 34, (2013) pp. 8511-8520.

De Boer, et al., "Improved signal-to-noise ratio in spectral-domain compared with time-domain optical coherence tomography" Optics Letters, vol. 28, No. 21, Nov. 1, 2003, pp. 2067-2069.

D'Andrea, et al., "Time-resolved optical imaging through turbid media using a fast data acquisition system based on a gated CCD camera" Journal of Physics D: Applied Physics, vol. 36, No. 14, Jul. 1, 2003, pp. 1675-1681.

Danielli, et al., "Label-free photoacoustic nanoscopy," Journal of Biomedical Optics, vol. 19, No. 8, Aug. 2014, pp. 086006-1-086006-10.

Dazzi, A. et al., "AFM-IR: technology and applications in nanoscale infrared spectroscopy and chemical imaging," Chem. Rev. 117, 5146-5173 (2017).

Dazzi, A., et al., "Local infrared microspectroscopy with subwavelength spatial resolution with an atomic force microscope tip used as a photothermal sensor," Optics Letters, vol. 30, No. 18, Sep. 15, 2005, pp. 2388-2390.

De Avila, et al., "Micromotor-enabled active drug delivery for in vivo treatment of stomach infection" Nat. Commun. 8: 272, (2017) pp. 1-9.

De Zerda, et al., "Family of enhanced photoacoustic imaging agents for high-sensitivity and multiplexing studies in living mice," ACS Nano 6(6), Jun. 26, 2012, pp. 4694-4701.

Deán-Ben, et al., "Functional optoacoustic neuro-tomography for scalable whole-brain monitoring of calcium indicators," Light Sci. Appl., vol. 5, No. 12, p. e16201, 2016, pp. 1-7.

Deán-Ben, et al., "Portable spherical array probe for volumetric real-time optoacoustic imaging at centimeter-scale depths," Opt. Express, vol. 21, No. 23, 2013, pp. 28062-28071.

Deserno, M., "How to generate equidistributed points on the surface of a sphere," Polym. Ed, p. 99, 2004, p. 1.

Diebold, et al., "Photoacoustic Monopole Radiation in One, Two and Three Dimensions," Physical Review Letters, Figs. 1 and 2, vol. 67, No. 24, Dec. 9, 1991 , pp. 3384-3387.

Diebold, et al., "Photoacoustic Signature of Particulate Matter: Optical Production of 9 Acoustic Monopole Radiation," Science New Series, Oct. 5, 1990, pp. 101-104, vol. 250, No. 4977, pp. 101-104.

Diem, M. et al., "Molecular pathology via IR and Raman spectral imaging." Journal of Biophotonics, vol. 6, No. 11-12 (2013) pp. 855-886. <doi:10.1002/jbio.201300131>.

Diem, M., et al., "A decade of vibrational micro-spectroscopy of human cells and tissue (1994-2004)†," Analyst, Oct. 2004, vol. 129, No. 10, pp. 880-885. <doi:10.1039/b408952a>.

Draeger, C., Fink, M., "One-channel time reversal of elastic waves in a chaotic 2D-silicon cavity," Phys. Rev. Lett. 79, 407-410 (Jul. 21, 1997).

Dunn, et al., "Transport-based image reconstruction in turbid media with small source-detector separations," Optics Letters, vol. 25, No. 24, Dec. 15, 2000, pp. 1777-1779.

Eghtedari, et al., "High Sensitivity of In Vivo Detection of Gold Nanorods Using a Laser Optoacoustic Imaging System," Nano Letters, vol. 7, No. 7, 2007, pp. 1914-1918.

Ermilov et al., "Laser optoacoustic imaging system for detection of breast cancer," Journal of Biomedical Optics, vol. 14 No. 2, pp. 24007-024007-14 (2009).

Erpelding et al., "Sentinel Lymph Nodes in the Rat: Noninvasive Photoacoustic and US Imaging with a Clinical US System," Radiology, 256(1): 102-110 (2010).

Evans, et al., "Coherent Anti-Stokes Raman Scattering Microscopy: Chemical Imaging for Biology and Medicine," Annual Review of Analytical Chemistry 1, (2008), pp. 883-909.

Fan, et al., "Development of a Laser Photothermoacoustic Frequency-Swept System for Subsurface Imaging: Theory and Experiment," J. Acoust. Soc. Am., vol. 116 (6), Dec. 2004, pp. 3523-3533.

Fan, et al., "Sub-Cellular Resolution Delivery of a Cytokine via Precisely Manipulated Nanowires" Nat. Nanotechnol. 5(7), Jul. 2010, 545-551. <doi:10.1038/nnano.2010.104>.

Fang, et al., "Photoacoustic Doppler effect from flowing small light-absorbing particles," Physical Review Letters 99(18) 184501-(1-4) (Nov. 2, 2007).

Fercher, et al., "Measurement of Intraocular Distances by Backscattering Spectral Interferometry," Optics Communications, 1995, vol. 117, pp. 43-48.

Fernandez, D. C., Bhargava, R., Hewitt, S. M. & Levin, I. W., "Infrared spectroscopic imaging for histopathologic recognition," Nat. Biotechnol. 23, 469-474 (2005).

Foster, et al., "Advances in ultrasound biomicroscopy" Ultrasound in Medicine & Biology, vol. 26, No. 1, Jan. 2000, pp. 1-27.

Fujita, K., et al., "Confocal multipoint multiphoton excitation microscope with microlens and pinhole arrays," Opt. Comm. 174, 7-12 (Jan. 15, 2000).

Furstenberg, et. al., "Chemical Imaging using Infrared Photothermal Microspectroscopy," In Proceedings of SPIE Defense, Security, and Sensing (eds Druy, M.A. & Crocombe, R. A.) 837411 (SPIE, 2012).

Gaihre, et al., "Gelatin-coated magnetic iron oxide nanoparticles as carrier system: Drug loading and in vitro drug release study," Int. J. Pharm. 365, (2009) pp. 180-189.

Gao, et al., "Single-shot compressed ultrafast photography at one hundred billion frames per second," Nature 516(7529) 74-77 (Dec. 4, 2014).

Gao, et al., "A review of snapshot multidimensional optical imaging: measuring photon tags in parallel" Phys Rep. 616, Feb. 29, 2016, pp. 1-37. <doi:10.1016/j.physrep.2015.12.004>.

Gao, et al., "Artificial micromotors in the mouse's stomach: A step toward in vivo use of synthetic motors," ACS Nano 9, (2015) pp. 117-123.

Gibson, et al., "Recent advances in diffuse optical imaging" Physics in Medicine and Biology 50, 2005, pp. R1-R43, Inslilule of Physics Publishing, UK.

Gong, L. et al., "Breaking the diffraction limit by saturation in stimulated-Raman-scattering microscopy: a theoretical study," Phys. Rev. A 90, 13818 (2014).

Griffiths, P., "Fourier transform infrared spectrometry," Science 21, 297-302 (1983).

Guggenheim, et al., "Ultrasensitive planoconcave optical microresonators for ultrasound sensing", Nat. Photon. 11, 714-721 (2017).

Guittet C, et al., "In vivo high-frequency ultrasonic characterization of human dermis" IEEE Transactions on Bio-medical Engineering. Jun. 1999;46(6):740-746. <doi:10.1109/10.764950>.

Guo, et al., "Calibration-free absolute quantification of optical absorption coefficients using acoustic spectra in three-dimensional photoacoustic microscopy of biological tissue" Opt Lett. 2010 ; 35(12): 2067-2069. <doi:10.1364/OL.35.002067>.

Guo, et al., "CsxWO3 nanorods coated with polyelectrolyte multilayers as a multifunctional nanomaterial for bimodal imaging-guided photothermal/photodynamic cancer treatment," Adv. Mater. 29, 1604157 (2017).

(56) References Cited

OTHER PUBLICATIONS

Haas, J. et al., "Advances in Mid-Infrared Spectroscopy for Chemical Analysis," Annu. Rev. Anal. Chem. 9 (2016) pp. 45-68.
Hai, et al., "Near-infrared optical-resolution photoacoustic microscopy", Opt. Lett. 39, 5192-5195 (Sep. 1, 2014).
Hai, et al., "High-throughput, label-free, single-cell photoacoustic microscopy of intratumoral metabolic heterogeneity," Nature Biomedical Engineering 3(5) 381-391 (May 2019).
Han, Y. et al., "Three-dimensional optoacoustic reconstruction using fast sparse representation," Opt. Lett., vol. 42, No. 5, (2017) pp. 979-982.
Han, et al., "Optoacoustic image reconstruction and system analysis for finite-aperture detectors under the wavelet-packet framework," J. Biomed. Opt., vol. 21, No. 1, Jan. 2016, pp. 016002-1-016002-9.
Hebden et al., "Enhanced time-resolved imaging with a diffusion model of photon transport" Optics Letters, vol. 19, No. 5, 1994, pp. 311-313.
Hee, et al., "Femtosecond transillumination tomography in thick tissues" Optics Letters, vol. 18, No. 13, 1993, pp. 1107-1109.
Hillman, et al., "Laminar optical tomography: demonstration of millimeter-scale depth-resolved imaging in turbid media," Optics Letters, vol. 29, No. 14, Jul. 15, 2004, pp. 1650-1652.
Hoelen, et al., "Three Dimensional Photoacoustic Imaging of Blood Vessels in Tissue" Optics Letters, 1998, pp. 648-650, vol. 23, No. 8, Optical Society of America, USA.
Hong, et al., "Simple Method to Produce Janus Colloidal Particles in Large Quantity" Langmuir 22, (2006) pp. 9495-9499.
Hu, C., et al., "Soft Micro- and Nanorobotics," Annu. Rev. Control. Robot. Auton. Syst. 1, (2018) pp. 53-75.
Hu, W., et al., "Small-scale soft-bodied robot with multimodal locomotion," Nature 554, 81-85, (2018).
Hu, S. et al., "Three-dimensional optical-resolution photoacoustic microscopy," Journal of Visualized Experiments 51 (2011).
Hu, S., et al., "Label-free Photoacoustic Ophthalmic Angiography" Optics Letters, 35(1), Jan. 1, 2010, pp. 1-3.
Huang, et al., "Aberration correction for transcranial photoacoustic tomography of primates employing adjunct image data," Journal of Biomedical Optics, vol. 17, No. 6, Jun. 2012, pp. 066016-1 to 066016-8.
Huang, et al., "Optical Coherence Tomography," Science, New Series, vol. 254, No. 5035, Nov. 22, 1991, pp. 1178-1181.
Huang, et al., "Full-wave iterative image reconstruction in photoacoustic tomography with acoustically inhomogeneous media," IEEE Trans. Med. Imaging, vol. 32, No. 6, Jun. 2013, pp. 1097-1110.
Huber, et al., "Three-Dimensional and C-Mode 6 OCT Imaging with a Compact, Frequency Swept Laser Source at 1300 nn" Optics Express, vol. 13, No. 26, Dec. 26, 2005, pp. 10523-10526.
Imai, T. et al., "High-throughput ultraviolet photoacoustic microscopy with multifocal excitation," Journal of Biomedical Optics 23(3), 036007 (Mar. 15, 2018).
Ing, R. K., Quieffin, N., Catheline, S., Fink, M., "In solid localization of finger impacts using acoustic time-reversal process," Appl. Phys. Lett. 87, 204104 (Nov. 14, 2005).
Ji, M. et al., "Detection of human brain tumor infiltration with quantitative stimulated Raman scattering microscopy," Sci. Transl. Med 7, 309ra163 (2015).
Ji, T. et al. "Preparation, Characterization, and Application of Au-Shell/Polystyrene Beads and Au-hell/Magnetic Beads" Adv. Mater. 13(16), Aug. 2001, pp. 1253-1256.
Karamata, et al., "Multiple Scattering in Optical Coherence Tomography I Investigation and Modeling" Journal of Optical Society of America, vol. 22, No. 7 (2005) pp. 1369-1379.
Karamata, et al., "Multiple scattering in optical coherence tomography. II. Experimental and theoretical investigation of cross talk in wide-field optical coherence tomography" J. Opt. Soc. Am. A/vol. 22, No. 7/Jul. 2005, pp. 1380-1388.
Karshalev, E. et al., "Micromotor Pills as a Dynamic Oral Delivery Platform" American Chemical Society Nano, 2018, vol. 12, No. 8, pp. 8397-8405 <DOI:10.1021/acsnano.8b03760>.

Kim, C. et al., "In vivo molecular photoacoustic tomography of melanomas targeted by bio-conjugated gold nanocages" ACS Nano, 2010; 4(8), pp. 4559-4564. <doi:10.1021/nn100736c>.
Kirch, J., et al., "Optical tweezers reveal relationship between micro structure and nanoparticle penetration of pulmonary mucus," Proc. Natl. Acad. Sci. 109, (2012) pp. 18355-18360.
Knoll, B. & Keilmann, F., "Near-field probing of vibrational absorption for chemical microscopy," Nature 399, 134-137 (1999).
Kole, M. R., et al., "Discrete frequency infrared microspectroscopy and imaging with a tunable quantum cascade laser," Anal. Chem. 84, 10366-10372 (2012).
Kolkman, et al., "In Vivo Photoacoustic Imaging of Blood Vessels Using an Extreme-Narrow Aperture Sensor" IEEE Journal of Selected Topics in Quantum Electronics, vol. 9, No. 2, Mar./Apr. 2003, pp. 343-346.
Koziolek, et al., "Navigating the human gastrointestinal tract for oral drug delivery: Uncharted waters and new frontiers," Adv. Drug Delivery Rev. 101, (2016) pp. 75-88.
R. A. Kruger, et al., "Dedicated 3D photoacoustic breast imaging," Med. Phys., vol. 40, No. 11, 2013, pp. 113301-1-113301-8.
Kruger et al., "Photoacoustic Ultrasound (PAUS)—Reconstruction Tomography" Med. Phys., Oct. 1995, vol. 22 (10) Am. Assoc. Phys. Med., USA, pp. 1605-1609.
Kruger, et al., "Thermoacoustic computed tomography—technical considerations" Medical Physics, 26(9): 1832-1837 (1999).
Kruger et al., "Thermoacoustic computed tomography using a conventional linear transducer array," Medical Physics, 30(5): 856-860 (2003).
Kruger, et al., "Thermoacoustic Molecular Imaging of Small Animals," Molecular Imaging, 2(2): 113-123 (2003).
Kruger, et al., "Thermoacoustic CT: imaging principles," Proc. SPIE 3916, (2000) pp. 150-160.
Kruger, et al., "Breast Cancer in Vivo: Contrast Enhancement with Thermoacoustic CT at 434 MHz-Feasibility Study," Radiology, 216(1): 279-283 (2000).
Ku and Wang, "Scanning thermoacoustic tomography in biological tissue." Medical physics 27.5 (2000): 1195-1202.
Ku and Wang, "Scanning microwave-induced thermoacoustic tomography: Signal, resolution, and contrast," Medical Physics, 28(1): 4-10 (2001).
Ku, G. et al., "Multiple-bandwidth photoacoustic tomography," Physics in Medicine & Biology, 49(7): 1329-1338 (2004).
Ku and Wang, "Deeply penetrating photoacoustic tomography in biological tissues enhanced with an optical contrast agent," Optics Letters, 30(5): 507-509 (2005).
Ku, et al., "Imaging of tumor angiogenesis in rat brains in vivo by photoacoustic tomography," Applied Optics, 44(5): 770-775 (2005).
Ku, et al., "Thermoacoustic and Photoacoustic Tomography of Thick Biological Tissues Toward Breast Imaging," Technology in Cancer Research & Treatment, 4(5): 559-566 (2005).
Kunitz, M., "Crystalline desoxyribonuclease; isolation and general properties; spectrophotometric method for the measurement of desoxyribonuclease activity," The Journal General Physiology, vol. 33, Mar. 20, 1950, pp. 349-362. <URL:http://doi.org./10.1085/jgp.33.4.349>.
Kuppusami, S. et al., "Parylene Coatings in Medical Devices and Implants: A Review" Universal Journal of Biomedical Engineering, 2015, vol. 3, No. 2, pp. 9-14 <DOI: 10.13189/ujbe.2015.030201>.
Lai, S. et al., "Mucus-penetrating nanoparticles for drug and gene delivery to mucosal tissues," Adv. Drug Deliv. Rev. 61(2), Feb. 27, 2009, pp. 158-171. <doi:10.1016/j.addr.2008.11.002>.
Lai, P. et al., "Photoacoustically guided wavefront shaping for enhanced optical focusing in scattering media," Nature Photonics 9 126-132 (Jan. 19, 2015).
Lai, P. et al., "Dependence of optical scattering from Intralipid in gelatin-gel based tissue-mimicking phantoms on mixing temperature and time" Journal of Biomedical Optics, vol. 19, No. 3, Mar. 2014, pp. 035002-1-035002-6.
Larina, et al., Real-time optoacoustic monitoring of temperature in tissues: Journal of Physics D: Applied Physics, vol. 38, (2005) pp. 2633-2639.
Lasch, et al., "FT-IR spectroscopic investigations of single cells on the subcellular level," Vibr. Spectrosc. 28, 147-157 (2002).

(56) References Cited

OTHER PUBLICATIONS

Laser Institute of America, "American National Standard for the safe use of lasers," American National Standard Institute (ANSI Z136.1-2007 Revision of ANSI Z136.1-2000).

Leal, et al., "Physicochemical properties of mucus and their impact on transmucosal drug delivery," Int. J. Pharm. 532, (2017) pp. 555-572.

Lewis, E. N. et al., "Fourier transform spectroscopic imaging using an infrared focal-Plane array detector," Anal. Chem. 67, 3377-3381 (1995).

Leitgeb, et al., "Performance of fourier domain vs. time domain optical coherence tomography," Optical Express, vol. 11, No. 8, Apr. 21, 2003, pp. 889-894.

Li, et al., "An Enteric Micromotor Can Selectively Position and Spontaneously Propel in the Gastrointestinal Tract," ACS Nano. 10(10), Oct. 25, 2016, pp. 9536-9542. <doi:10.1021/acsnano.6b04795>.

Li, et al., "Autonomous Collision-Free Navigation of Microvehicles in Complex and Dynamically Changing Environments" ACS Nano, 11, (2017) pp. 9268-9275.

Li, G., et al., "Reflection-mode multifocal optical-resolution photoacoustic microscopy," J. Biomed. Opt. 18, 030501 (Feb. 12, 2013).

Li, J. et al., "Micromotors Spontaneously Neutralize Gastric Acid for pH-Responsive Payload Release" Angewandte Chemie International Edition, vol. 56, No. 8, 2017, pp. 2156-2161. <DOI: 10.1002/anie.201611774>.

Li, L., et al., "Small near-infrared photochromic protein for photoacoustic multi-contrast imaging and detection of protein interactions in vivo," Nature Communications 9(1) 2734 (Jul. 16, 2018).

Li, et al., "Single-impulse panoramic photoacoustic computed tomography of small-animal whole-body dynamics at high spatiotemporal resolution," Nat Biomed Eng. 1(5) May 2017, pp. 1-11. <doi:10.1038/s41551-017-0071>.

Li, L.., et al., "Simultaneous Molecular and Hypoxia Imaging of Brain Tumors in Vivo Using Spectroscopic Photoacoustic Tomography," Proceedings of the IEEE, 96(3): 481-489 (2008).

Li, J. et al., "Micro/Nanorobots for Biomedicine: Delivery, Surgery, Sensing, and Detoxification" Sci Robot, 2(4), Mar. 15, 2017, pp. 1-20. <doi:10.1126/scirobotics.aam6431>.

Li, Y. et al., "Multifocal photoacoustic microscopy through an ergodic relay (Conference Presentation)", Proc. SPIE 10878, Photons Plus Ultrasound: Imaging and Sensing 2019, 108781C, presented Feb. 4, 2019, published Mar. 4, 2019, https://doi.org/10.1117/12.2513502.

Li, et al., "Optical Coherence Computed Tomography," Applied Physics Letters, vol. 91, American Institute of Physics, 2007, pp. 141107-1-141107-3.

Li, et al., "Snapshot photoacoustic topography through an ergodic relay for high-throughput imaging of optical absorption," Nature Photonics 14(3) (2020) pp. 164-170. <URL:https://doi.org/10.1038/s41566-019-0576-2>.

Li, Z., et al., "Super-resolution far-field infrared imaging by photothermal heterodyne imaging," The Journal of Physical Chemistry B, vol. 121 (2017) pp. 8838-8846.

Li, Z., et al., "Super-resolution imaging with mid-IR photothermal microscopy on the single particle level," In Proceedings of SPIE Physical Chemistry of Interfaces and Nano-materials XIV, vol. 9549, Aug. 20, 2015, pp. 954912-1-954912-8.

Liang, et al., "Single-shot real-time femtosecond imaging of temporal focusing," Light-Science & Applications 7(1) 42 (Aug. 8, 2018).

Liang, et al., "Single-shot real-time video recording of a photonic Mach cone induced by a scattered light pulse," Science Advances 3(1) e1601814 (Jan. 20, 2017).

Liang, et al., "Single-shot ultrafast optical imaging," Optica 5(9) 1113-1127 (Sep. 2018).

Lin, et al., "Single-breath-hold photoacoustic computed tomography of the breast," Nature Communications 9(1) 2352 (Jun. 15, 2018).

Liu, et al., "Optical focusing deep inside dynamic scattering media with near-infrared time-reversed ultrasonically encoded (TRUE) light," Nature Communications 6 5409 (Jan. 5, 2015).

Liu, et al., "Label-free cell nuclear imaging by Grüneisen relaxation photoacoustic microscopy" Opt Lett. Feb. 15, 2018; 43(4), (2018) pp. 947-950.

Lovell, et al., "Porphysome nanovesicles generated by porphyrin bilayers for use as multimodal biophotonic contrast agents," Nature Materials 10(4) 324-32 (Mar. 20, 2011).

Lu, F., et al., "Tip-enhanced infrared nanospectroscopy via molecular expansion force detection," Nat. Photon. 8, 307-312 (2014).

Lu, F.-K. et al., "Label-free DNA imaging in vivo with stimulated Raman scattering microscopy," Proc. Natl Acad Sci. USA 112, 11624-11629 (2015).

Ma, et al., "Time-reversed adapted-perturbation (TRAP) optical focusing onto dynamic objects inside scattering media," Nature Photonics 8(12) 931-936 (Nov. 2, 2014).

Manohar, et al., "Initial results of in vivo non-invasive cancer imaging in the human breast using near-infrared pho to acoustics," Optics Express, 15(19): 12277-12285 (2007).

Maslov, et al., "In vivo dark-field reflection-mode photoacoustic microscopy," Optics Letters 30(6), Mar. 15, 2005, pp. 625-627.

Maslov, et al., "Optical-resolution photoacoustic microscropy for in vivo imaging of single capillaries," Optical Letters, 33(9): 929-931 (2008).

Maslov, et al., "Photoacoustic Imaging of biological tissue with Intensity-Modulated Continuous-Wave Laser" Journal of Biomedical Optics, 2008, pp. 024006 1-5, vol. 13(2), SPIE, USA.

Matthews, et al., "Parameterized Joint Reconstruction of the Initial Pressure and Sound Speed Distributions for Photoacoustic Computed Tomography," SIAM J. Imaging Sci., vol. 11, No. 2, (2018) pp. 1560-1588.

Matsumoto, et al., "Label-free photoacoustic imaging of human palmar vessels: a structural morphological analysis," Sci. Rep., vol. 8, No. 1, (2018) p. 786.

Medina-Sanchez, et al., "Medical microbots need better imaging and control," Nature 545, (2017) pp. 406-408.

Michaelian, Kirk H. "Photoacoustic IR spectroscopy: instrumentation, applications and data analysis" John Wiley & Sons; Dec. 1, 2010. <Preface Only>.

Miller, et al., "Synchrotron-based biological microspectroscopy: From the mid-infrared through the far-infrared regimes," Journal of Biological Physics 29, 219-230 (2003).

Mishra et al., "Development and comparison of the DTM, the DOM and the FVM formulations for the short-pulse laser transport through a participating medium" International Journal of Heat and Mass Transfer, vol. 49 (2006) pp. 1820-1832.

Mitsuhashi, et al., "A forward-adjoint operator pair based on the elastic wave equation for use in transcranial photoacoustic computed tomography," SIAM J. Imaging Sci., vol. 10, No. 4, 2017, pp. 2022-2048.

Mitsuhashi, et al., "Investigation of the far-field approximation for modeling a transducer's spatial impulse response in photoacoustic computed tomography," Photoacoustics, vol. 2, No. 1, 2014, pp. 21-32.

Montaldo, et al., "Building three-dimensional images using time-reversal chaotic cavity", IEEE Trans. Ultrason. Ferroelectr. Freq. Control 52, pp. 1489-1497 (2005).

Morgner et al., "Spectroscopic optical coherence tomography," Optics Letters, vol. 25, No. 2, Jan. 15, 2000, pp. 111-113.

Murray et al., "High-Sensitivity Laser-Based Acoustic Microscopy Using a Modulated Excitation Source," Applied Physics Letters, vol. 85, No. 14, American Institute of Physics, USA., Oct. 4, 2004, pp. 2974-2976.

Nakajima, et al., "Three-dimensional analysis and classification of arteries in the skin and subcutaneous adipofascial tissue by computer graphics imaging," Plastic and Reconstructive Surgery, 102(3): 748-760 (1998).

Nasiriavanaki, et al., "High-resolution photoacoustic tomography of resting-state functional connectivity in the mouse brain," Proceedings of the National Academy of Sciences 111(1) 21-26 (Jan. 7, 2014).

(56) References Cited

OTHER PUBLICATIONS

Nasse, M. J. et al., "High-resolution Fourier-transform infrared chemical imaging with multiple synchrotron beams," Nat. Methods 8, 413-416 (2011).
Nelson et al., "Imaging Glioblastoma Multiforme," The Cancer Journal vol. 9, No. 2, Mar./Apr. 2003, pp. 134-145.
Niederhauser et al., "Combined Ultrasound and Optoacoustic System for Real-Time High-Contrast Vascular imaging in Vivo," IEEE Transactions on MedicalImaging, 24(4): 436-440 (2005).
Nowak, D. et al., "Nanoscale chemical imaging by photoinduced force microscopy," Sci. Adv. 2, Mar. 25, 2016, e1501571, pp. 1-9.
Ntziachristos, V., "Going deeper than microscopy: the optical imaging frontier in biology" Nature Methods vol. 7, No. 8, Aug. 2010, pp. 603-614.
Ogunlade, et al., "In vivo three-dimensional photoacoustic imaging of the renal vasculature in preclinical rodent models," Am. J. Physiol.-Ren. Physiol., vol. 314, No. 6, (2018) pp. F1145-F1153.
Oraevsky et al., "Optoacoustic Tomography," Biomedical Photonics Handbook, 2003, chapter 34: pp. 931-964, CRC Press LLC, USA.
Oraevsky et al., "Ultimate Sensitivity of Time-Resolved Opto-Acoustic Detection," Biomedical Optoacoustics, 2000, pp. 228-239, vol. 3916, SPIE, USA.
Oraevsky et al., "Laser Optoacoustic Tomography of Layered Tissues: Signal Processing" Proceedings of SPIE, 2979: 59-70 (1997).
Oraevsky et al., "Laser opto-acoustic imaging of the breast: Detection of cancer angiogenesis" Proceedings of SPIE, 3597: 352-363 (1999).
Patel, et al., "Pulsed optoacoustic spectroscopy of condensed matter," Rev. Mod. Phys., vol. 53 (1981) pp. 517-550.
Paxton, et al., "Catalytic nanomotors: Autonomous movement of striped nanorods," J. Am. Cherm. Soc. 126, 13424-13431 (2004).
Petrov, et al., "Optoacoustic, Noninvasive, Real-Time, Continuous Monitoring of Cerebral Blood Oxygenation: An In Vivo Study in Sheep" Anesthesiology, vol. 102, No. 1, Jan. 2005, pp. 69-75.
Potter, et al., "Capillary diameter and geometry in cardiac and skeletal muscle studied by means of corrosion casts" Microvascular Research, 25(1): 68-84 (1983).
Pramanik, M., "Improving tangential resolution with a modified delayand-sum reconstruction algorithm in photoacoustic and thermoacoustic tomography," JOSA A, vol. 31, No. 3, (2014) pp. 621-627.
Prati, et al., "New advances in the application of FTIR microscopy and spectroscopy for the characterization of artistic materials," Accounts of Chemical Research, vol. 43, (2010) pp. 792-801.
Prevedel, et al., "Simultaneous whole-animal 3D imaging of neuronal activity using light-field microscopy," Nat. Methods 11, 727-730 (Jul. 2014).
Quickenden, et al., "The ultraviolet absorption spectrum ofliquid water," J Chem. Phys. 72, 4416-4428 (1980).
Razansky, et al., "Multispectral opto-acoustic tomography of deep-seated fluorescent proteins in vivo," Nature Photonics 3, (2009) pp. 412-417.
Robert et al., "Fabrication of Focused Poly (Vinylidene Fluoride-Trifluoroethylene) P19 (VDF-TrFE) Copolymer 40-50 MHz Ultrasound Transducers on Curved Surfaces," Journal of Applied Physics, vol. 96, No. 1. Jul. 1, 2004, pp. 252-256.
Rockley, M.G., "Fourier-transformed infrared photoacoustic spectroscopy of polystyrene film," Chem. Phys. Lett. 68, 455-456 (1979).
Rosenblum, et al., "Progress and challenges towards targeted delivery of cancer therapeutics" Nat. Commun. 9, (2018) 1410, pp. 1-12.
Saager et al., "Direct characterization and removal of interfering absorption trends in two-layer turbid media" J. Opt. Soc. Am. A, vol. 22, No. 9, Sep. 2005, pp. 1874-1882.
Sanchez, et al., "Chemically powered micro- and nanomotors," Angew. Chem. Int. Ed. 54, (2015) pp. 1414-1444.
Sakadzic, et al., "Correlation transfer and diffusion of ultrasound-modulated multiply scattered light," Physical Review Letters 96(16) 163902-(1-4) (Apr. 28, 2006).

Savateeva, et al., "Noninvasive detection and staging or oral cancer in vivo with confocal opto-acoustic tomography" Biomedical Optoacoustics, vol. 3916, International Society for Optics and Photonics 2000, pp. 55-66.
Schambach, et al., "Application of micro-CT in small animal imaging" Methods, vol. 50, No. 1, Jan. 2010, pp. 2-13.
Schmidt, et al., "A 32-Channel Time Resolved Instrument for Medical Optical Tomography" Review of Scientific Instruments, vol. 71, No. 1, Jan. 2000, pp. 256-265.
Scholte, et al., "On spatial sampling and aliasing in acoustic imaging" 12th Intern. congress on sound and vibration, Lisbon, Portugal (2005) pp. 1-8.
Schoeder, et al., "Optoacoustic image reconstruction: the full inverse problem with variable bases," Proc. R. Soc. A, vol. 474, No. 2219, (2018) pp. 1-20.
Schroeter, et al., "Spontaneous slow hemodynamic oscillations are impaired in cerebral microangiopathy," Journal of Cerebral Blood Flow & Metabolism (2005) 25, pp. 1675-1684.
Servant, et al., "Controlled In Vivo Swimming of a Swarm of Bacteria-Like Microrobotic Flagella" Advanced Materials 27, (2015) pp. 2981-2988.
Sezer, et al., "Review of magnesium-based biomaterials and their applications," J. Magnesium Alloys 6, (2018) pp. 23-43.
Sethuraman et al., "Development of a combined intravascular ultrasound and photoacoustic imaging system" Proceedings of SPIE, 6086: 60860F.1-60860F.10 (2006).
Sethuraman et al., "Intravascular photoacoustic imaging of atherosclerotic plaques: Ex vivo study using a rabbit model of atherosclerosis" Proceedings of SPIE, 6437: 643729.1-643729.9 (2007).
Shah, J. et al., "Photoacoustic imaging and temperature measurement for photothermal cancer therapy," Journal of Biomedical Optics, vol. 13, No. 3, (May/Jun. 2008) pp. 034024-1-034024-9.
Sheth, et al., "Columnar Specificity of Microvascular Oxygenation and Volume Responses: Implications for Functional Brain Mapping," The Journal of Neuroscience, vol. 24, No. 3, Jan. 21, 2004, pp. 634-641.
Shi, J., et al., "High-resolution, high-contrast mid-infrared imaging of fresh biological samples with ultraviolet-localized photoacoustic microscopy," Nature Photonics 13 609-615 (May 2019).
Shmueli, et al., "Low Frequency Fluctuations in the Cardiac Rate as a Source of Variance in the Resting-State fMRI BOLD Signal," Neuroimage, vol. 38, No. 2, Nov. 1, 2007, pp. 306-320.
Silva, et al., "Toward Label-Free Super-Resolution Microscopy," ACS Photon. 3, 79-86 (2016).
Sim, et al., "In vivo Microscopic Photoacoustic Spectroscopy for Non-Invasive Glucose Monitoring Invulnerable to Skin Secretion Products," Sci. Rep. 8, 1059 (2018).
Siphanto et al., "Imaging of Small Vessels Using Photoacoustics: an in Vivo Study," Lasers in Surgery and Medicince, vol. 35, Wiley-Liss, Inc., Netherlands, Dec. 20, 2004, pp. 354-362.
Sitti, M., "Miniature soft robots-road to the clinic," Nat. Rev. Mater, 3, (2018) pp. 74-75.
Smith, et al., "Beyond C, H, O, and Ni analysis of the elemental composition of U.S. FDA approved drug architectures," J. Med. Chem. 57, pp. 9764-9773 (2014).
Sommer, A. J., et al., "Attenuated total internal reflection infrared mapping micro spectroscopy using an imaging microscope," Appl. Spectrosc. 55, 252-256 (2001).
Song, et al., "Fast 3-D dark-field reflection-mode photoacoustic microscopy in vivo with a 30-MHz ultrasound linear array" Journal of Biomedical Optics, 13(5): 054028.1-054028.5 (2008).
Song, et al., "Multi-focal optical-resolution photoacoustic microscopy in vivo." NIH Public Access Author Manuscript, May 13, 2011. pp. 1-7.
Song, et al., "Section-illumination photoacoustic microscopy for dynamic 3D imaging of microcirculation in vivo" Optics Letters, 35(9): 1482-1484 (2010).
Soppimath, et al., "Microspheres as floating drug-delivery systems to increase gastric retention of drugs" Drug Metab. Rev. 33, (2001) pp. 149-160.
Steinbrink, et al., "Illuminating the BOLD signal: combined fMRI-fNIRS studies" Magnetic Resonance Imaging, vol. 24, No. 4, May 2006, pp. 495-505.

(56) References Cited

OTHER PUBLICATIONS

Stern, MD., "In vivo evaluation of microcirculation by coherent light scattering," Nature, 254(5495): 56-58 (1975).
Tay, et al., "Magnetic Particle Imaging Guided Heating In Vivo using Gradient Fields for Arbitrary Localization of Magnetic Hyperthermia Therapy" ACS Nano. 12(4), Apr. 24, 2018, pp. 3699-3713. <doi:10.1021/acsnano.8b00893>.
Tam, A. C., "Applications of photoacoustic sensing techniques," Reviews of Modern Physics, vol. 58, No. 2, Apr. 1986, pp. 381-431.
Tearney, et al., "Scanning single-mode fiber optic catheter-endoscope for optical coherence tomography" Optics Letters, 21(7): 543-545 (1996).
Tran, et al., "In vivo endoscopic optical coherence tomography by use of a rotational microelectromechanical system probe" Optics Letters, 29(11): 1236-1238 (2004).
Treeby B. E., et al., "Photoacoustic tomography in absorbing acoustic media using time reversal," Inverse Probl. (2010) 26(11), pp. 1-20.
Treeby, et al., "k-Wave: MATLAB toolbox for the simulation and reconstruction of photoacoustic wave fields," J. Biomed. Opt., vol. 15, No. 2, Mar./Apr. 2010, pp. 021314.
Treeby, et al., "Advanced photoacoustic image reconstruction using the k-Wave toolbox," in Photons Plus Ultrasound: Imaging and Sensing 2016, 2016, vol. 9708, p. 97082P.
Tu, et al., "Self-propelled supramolecular nanomotors with temperature-responsive speed regulation," Nat. Chem. 9, 480 (2016).
Tzoumas, et al., "Eigenspectra optoacoustic tomography achieves quantitative blood oxygenation imaging deep in tissues," Nat. Commun., vol. 7, 2016, pp. 1-10.
Van Essen, et al., "An Integrated Software Suite for Surface-based Analyses of Cerebral Cortex" Journal of the American Medical Informatics Association, vol. 8, No. 5, Sep./Oct. 2001, pp. 443-459.
Velasco, E., "Ultrafast Camera Takes 1 Trillion Frames Per Second of Transparent Objects and Phenomena" [Webpage] Caltech, California Institute of Technology, Jan. 17, 2020, pp. 1-2. <URL:https://www.eurekalert.org/pub_releases/2020-01/ciot-uct012120.php>.
Viator et al., "Design testing of an endoscopic photoacoustic probe for determination of treatment depth after photodynamic therapy" Proceedings of SPIE in Biomedical Optoacoustics II, 4256: 16-27 (2001).
Vilela, et al., "Medical imaging for the tracking of micromotors," ACS Nano 12, (2018) pp. 1220-1227.
Wang, et al., "Ballistic 2-D Imaging Through Scattering Walls Using an Ultrafast Optical Kerr Gale," Science, vol. 253, Aug. 16, 1991, pp. 769-771.
Wang, et al., "Biomedical Optics, Principles and Imaging," Wiley-Interscience, A John Wiley & Sons, Inc., (2007) p. 7.
Wang et al., "Biomedical optics: principles and imaging," Section 12.5; Photoacoustic Tomography, John Wiley & Sons (2012) pp. 288-290.
Wang, et al., "Fabrication of micro/nanoscale motors" Chem. Rev. 115, (2015) pp. 8704-8735.
Wang, B. et al., "Recent progress on micro- and nano-robots: towards in vivo tracking and localization" Quantitative Imaging in Medicine and Surgery, 2018, vol. 8, No. 5, pp. 461-479. <DOI: 10.21037/qims.2018.06.07>.
Wang, L. et al., "Grueneisen relaxation photoacoustic microscopy," Physical Review Letters 113 174301 (Oct. 24, 2014).
Wang, L. V & Yao, J., "A practical guide to photoacoustic tomography in the life sciences," Nat. Methods 13, 627-638 (Jul. 28, 2016).
Wang, L. V., "Multiscale photoacoustic microscopy and computed tomography," Nat. Photon. 3, 503-509 (Aug. 29, 2009).
Wang, L. V.; "Mechanisms of ultrasonic modulation of multiply scattered coherent light: an analytic model," Physical Review Letters 87(4) 043903-(1-4) (Jul. 23, 2001).
Wang, L. V.; "Prospects of photoacoustic tomography," Medical Physics 35(12), Nov. 19, 2008, pp. 5758-5767.
Wang, L., et al., "Single-cell label-free photoacoustic flowoxigraphy in vivo," Proceedings of the National Academy of Sciences 110(15) 5759-5764 (Apr. 9, 2013).
Wang, L., et al., "Ultrasonically encoded photoacoustic flowgraphy in biological tissue," Physical Review Letters 111(20), 204301 (Nov. 15, 2013).
Wang, L.V., Hu, S. "Photoacoustic Tomography: in vivo imaging from organelles to organs," Science 335, 1458-1462 (Mar. 23, 2012).
Wang, X. D., et al., "Noninvasive laser-induced photoacoustic tomography for structural and functional in vivo imaging of the brain," Nature Biotechnology 21(7) 803-806 (Jul. 2003).
Wang, et al., "MCML—Monte Carlo modeling of light transport in multilayered tissues" Computer Methods and Programs in Biomedicine, vol. 47, No. 2, Jul. 1995, pp. 131-146.
Wang et al., "Three-dimensional laser-induced photoacoustic tomography of mouse brain with the skin and skull intact," Optics Letters, 28(19): 1739-1741 (2003).
Wang et al., "Noninvasive photoacoustic angiography of animal brains in vivo with near-infrared light and an optical contrast agent" Optics Letters, 29(7): 730-732 (2004).
Wang, et al., "Intravascular Photoacoustic Imaging" IEEE J Quantum Electronics, 16(3): 588-599 (2010).
Wang, et al., "Nano/microscale motors: biomedical opportunities and challenges," ACS Nano 6, (2012) pp. 5745-5751.
Wang, K. et al., "Investigation of iterative image reconstruction in three-dimensional optoacoustic tomography," Phys. Med. Biol., vol. 57, No. 17, 2012, p. 5399-5423.
Wetzel, et al., "Imaging molecular chemistry with infrared microscopy," Science, New Series, vol. 285, No. 5431, Aug. 20, 1999, pp. 1224-1225.
Wong, T. et al., "Fast label-free multilayered histology-like imaging of human breast cancer by photoacoustic microscopy," Sci. Adv. 3, 1602168 (May 17, 2017).
Wong, T. et al., "Label-free automated three-dimensional imaging of whole organ by microtomy-assisted photoacoustic microscopy," Nat. Comm. 8, (Nov. 9, 2017).
Wu, Z., et al., "A microrobotic system guided by photoacoustic computed tomography for targeted navigation in intestines in vivo," Science Robotics 4(32) eaax0613 (Jul. 24, 2019).
Wu, D., et al., "In vivo Mapping of Macroscopic Neuronal Projections in the Mouse Hippocampus using High-resolution Diffusion MRI," Neuroimage 125, Jan. 15, 2016, pp. 84-93.
Xia, J., et al., "Photoacoustic tomography: principles and advances," Electromagn. Waves 147, 1 (2014; available in PMC Jan. 30, 2015).
Xia, J., et al., "Wide-field two-dimensional multifocal optical-resolution photoacoustic-computed microscopy," Opt. Lett. 38(24), Dec. 15, 2013, pp. 5236-5239.
Xu, et al., "Exact frequency-domain reconstruction for thermoacoustic tomography—II: Cylindrical geometry," IEEE Trans. Med. Imaging, vol. 21, No. 7, (2002) pp. 829-833.
Xu, et al., "Photoacoustic Imaging in Biomedicine," Review of Scientific Instruments, American Institute of Physics, vol. 77 (2006) pp. 041101 1-041101 22.
Xu, et al., "Rhesus monkey brain imaging through intact skull with thermoacoustic tomography," IEEE Trans. Ultrason. Ferroelectr. Freq. Control, vol. 53, No. 3, Mar. 2006, pp. 542-548.
Xu, et al., "Time-domain reconstruction for thermoacoustic tomography in a spherical geometry," IEEE Transactions on Medical Imaging 21(7) 814-822 (Jul. 2002).
Xu, et al., "Universal back-projection algorithm for photoacoustic computed tomography," Physical Review E 71(1) 016706-(1-7) (Jan. 19, 2005).
Xu, S., et al., "Thermal expansion of confined water," Langmuir 25, 5076-5083 (2009).
Xu, X. et al., "Time-reversed ultrasonically encoded optical focusing into scattering media," Nature Photonics 5(3) 154-157 (Jan. 16, 2011).
Xu, et al., "Time reversal and its application to tomography with diffracting sources," Physical Review Letters 92(3) 033902-(1-4) (Jan. 23, 2004).

(56) References Cited

OTHER PUBLICATIONS

Xu et al. "Time Reversal Ultrasound Modulated Optical Tomography Using a BSO Phase Conjugate Mirror," poster presented at SIPE Conference 7177 on Jan. 26, 2009, 1 page.
Yadlowsky, et al., "Multiple scattering in optical coherence microscopy" Applied Optics, vol. 34, No. 25 (1995) pp. 5699-5707. <doi.org/10.1364/AO.34.005699>.
Yan, et al., "Multifunctional biohybrid magnetite microrobots for imaging-guided therapy" Yan et al., Sci. Robot. 2, eaaq1155, Nov. 22, 2017, pp. 1-14.
Yang, "Optical coherence and Doppler tomography for monitoring tissue changes induced by laser thermal therapy—An in vivo feasibility study" Review of Scientific Instruments , vol. 74, No. 1, Jan. 2003, p. 437-440.
Yang, J. M. et al., "Simultaneous functional photoacoustic and ultrasonic endoscopy of internal organs in vivo," Nature Medicine 18(8) 1297-1303 (Aug. 2012).
Yang, J., et al., "Motionless volumetric photoacoustic microscopy with spatially invariant resolution," Nature Communications 8(1) 780 (Oct. 3, 2017).
Yang, et al., "Novel biomedical imaging that combines intravascular ultrasound (IVUS) and optical coherence tomography (Oct)" IEEE International Ultrasonics Symposium, Beijing, China, Nov. 2-5, 2008, pp. 1769-1772.
Yang, et al., "Time-reversed ultrasonically encoded optical focusing using two ultrasonic transducers for improved ultrasonic axial resolution" Journal of Biomedical Optics 18(11), 110502 (Nov. 2013) pp. 110502-1-110502-4.
Yang, et al., "The grand challenges of science robotics," Science Robotics 3, Jan. 31, 2018, eaar7650, pp. 1-14.
Yang, J.M., et al., "Focusing light inside live tissue using reversibly switchable bacterial phytochrome as a genetically encoded photochromic guide star" Science Advances 5(12) (2019) pp. 1-9.
Yao, et al., "Monte Carlo simulation of an optical coherence tomography signal in homogeneous turbid media" Phys. Med. Biol. 44(9), Jul. 8, 1999, pp. 2307-2320.
Yao, et al., "Absolute photoacoustic thermometry in deep tissue," Opt. Lett. 38, 5228-5231 (2013).
Yao, et al., "In vivo label-free photoacoustic microscopy of cell nuclei by excitation of DNA and RNA," Opt. Lett. 35, 4139-4141 (2010).
Yao, et al., "Optimal ultraviolet wavelength for in vivo photoacoustic imaging of cell nuclei," J Biomed. Opt. 17, 056004 (2012).
Yao, et al., "Photoimprint photoacoustic microscopy for three-dimensional label-free sub-diffraction imaging," Physical Review Letters 112(1) 014302 (Jan. 10, 2014).
Yao, L. et al., "Multiscale photoacoustic tomography using reversibly switchable bacterial phytochrome as near-infrared photochromic probe," Nature Methods 13(1) 67-73 (Jan. 2016).
Yao, L. et al., "High-speed label-free functional photoacoustic microscopy of mouse brain in action," Nat. Methods 12(5), 407-410 (May 12, 2015).
Yao, L. et al., "Photoacoustic microscopy: superdepth, superresolution, and superb contrast", IEEE Pulse 6, 34-7 (May 13, 2015).
Yaqoob, et al., "Methods and application areas of endoscopic optical coherence tomography" Journal of Biomedical Optics, 11(6): 063001.1-063001.19 (2006).
Yavuz, M. S., et al., "Gold nanocages covered by smart polymers for controlled release with near-infrared light," Nature Materials 8(12) 935-939 (Nov. 1, 2009).
Yin, et al., "Agarose particle-templated porous bacterial cellulose and its application in cartilage growth in vitro" Acta Biomater. 12, Jan. 2015, pp. 129-138. <doi:10.1016/j.actbio.2014.10.019>.
Yodh et al., "Functional Imaging with Diffusing Light" Biomedical Photonics Handbook, 2003, Ch. 21 , pp. 45, CRC Press, Boca Raton.
Yodh, et al. "Spectroscopy and Imaging with Diffusing Light" Physics Today 48(3), Mar. 1995, pp. 34-40.
Zeff, et al., "Retinotopic mapping of adult human visual cortex with high-density diffuse optical tomography" PNAS, vol. 104, No. 29, Jul. 17, 2007, pp. 12169-12174.
Zemp, et al., "Realtime photoacoustic microscopy in vivo with a 30MHZ ultrasonic array transducer" Optics Express, 16(11): 7915-7928 (2008).
Zhang, C., et al., "Coherent Raman scattering microscopy in biology and medicine," Annu. Rev. Biomed. Eng. 17, 415-445 (2015).
Zhang, D. et al., "Depth-resolved mid-infrared photothermal imaging of living cells and organisms with submicrometer spatial resolution," Sci. Adv. 2, e1600521 (2016).
Zhang, H. F. et al., "Functional photoacoustic microscopy for high-resolution and noninvasive in vivo imaging," Nature Biotechnology 24(7) 848-851 (Jul. 2006).
Zhang, H. F. et al., "In vivo imaging of subcutaneous structures using functional photoacoustic microscopy," Nature Protocols 2(4) 797-804 (Apr. 5, 2007).
Zhang, et al., "Intrinsic Functional Relations Between Human Cerebral Cortex and Thalamus" Journal of Neurophysiology, vol. 100, No. 4, Oct. 2008, pp. 1740-1748.
Zharov, et al., "In vivo photoacoustic flow cytometry for monitor of circulating single cancer cells and contrast agents," Optics Letters, 31(24): 3623-3625 (2006).
Zhou, et al., "Tutorial on photoacoustic tomography," J. Biomed. Opt., vol. 21, No. 6, Jun. 2016, pp. 061007-1-061007-14.
Zou, et al., "BOLD responses to visual stimulation in survivors of childhood cancer" NeuroImage, vol. 24, No. 1, Jan. 1, 2005, pp. 61-69.
U.S. Appl. No. 17/090,752, filed Nov. 5, 2020, Wang et al.
U.S. Office Action dated Apr. 7, 2022, in U.S. Appl. No. 16/560,680.

\* cited by examiner

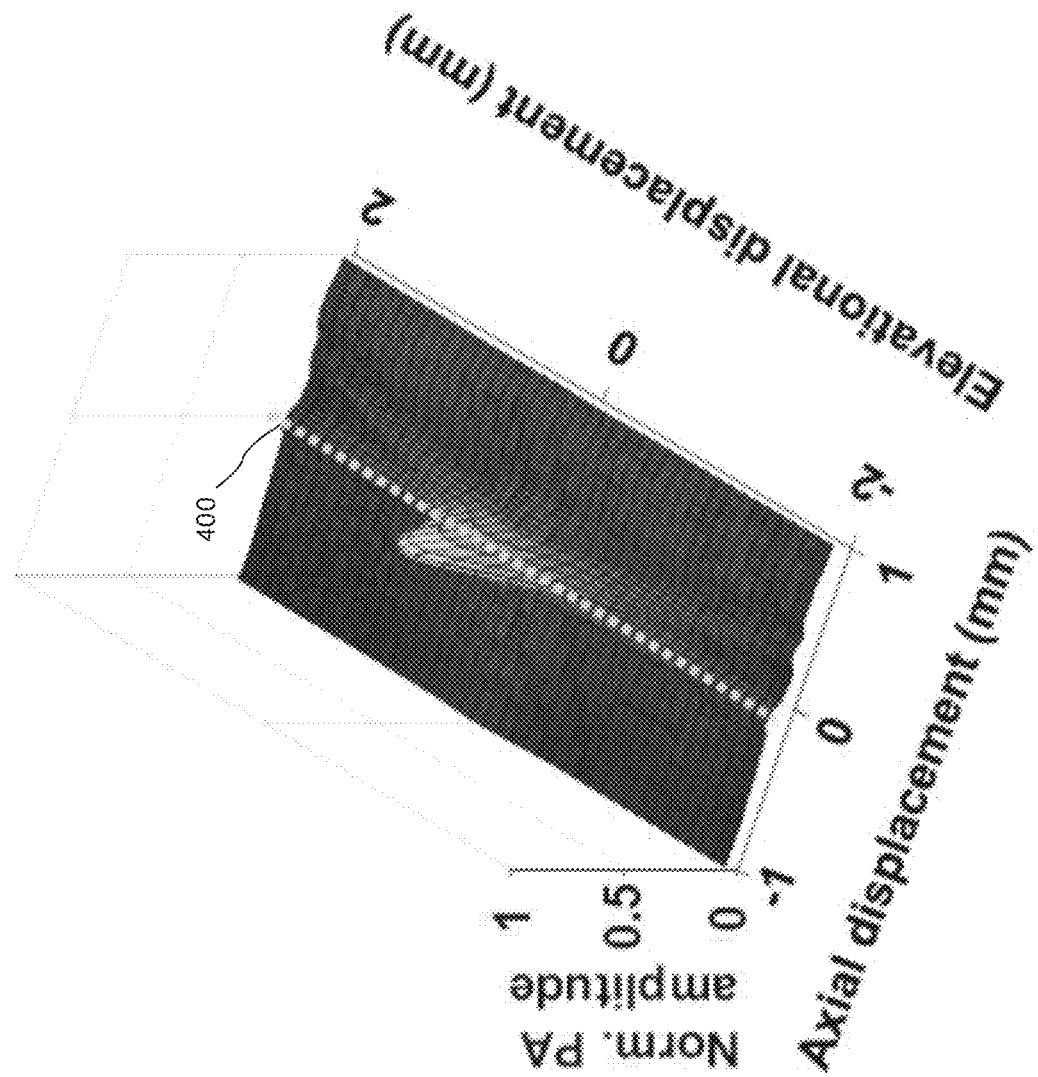
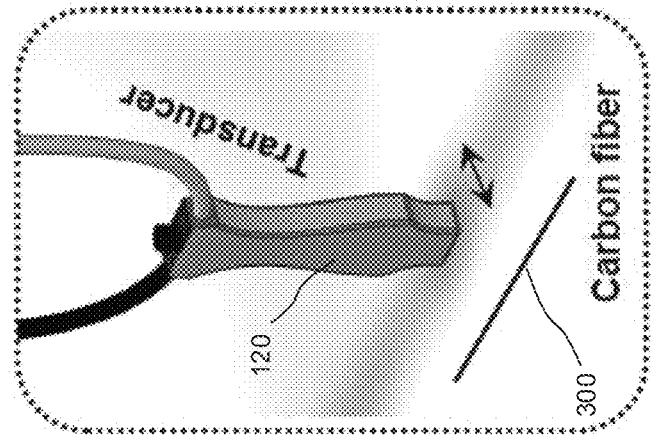
FIG. 4A
FIG. 4B

VELOCITY-MATCHED ULTRASONIC TAGGING IN PHOTOACOUSTIC FLOWGRAPHY

CROSS-REFERENCES TO RELATED APPLICATIONS

This application claims priority to and benefit of U.S. Provisional Patent Application No. 62/812,426, titled "Velocity-Matching Ultrasonically Tagged Photoacoustic Lymphatic Flowgraphy (VMUT-PALF)" and filed on Mar. 1, 2019, which is hereby incorporated by reference in its entirety and for all purposes.

FEDERALLY SPONSORED RESEARCH OR DEVELOPMENT

This invention was made with government support under Grant No. NNX16A069A awarded by NASA. The government has certain rights in the invention.

FIELD

Certain embodiments generally relate to photoacoustic flowgraphy and, more specifically, certain aspects pertain to velocity-matched ultrasonic tagging in photoacoustic flowgraphy.

BACKGROUND

The lymphatic system is an essential part of both the immune and the circulatory systems. In the immune system, it removes invading microorganisms and defends against diseases. In the circulatory system, it maintains the interstitial fluid balance and absorbs fats and fat-soluble vitamins. It collects the excess interstitial fluid and returns them to blood in an open and low-pressure network. This characteristic makes the lymphatic flow vulnerable to microgravity, which may result in immune dysfunctions and fluid shifts in astronauts. The fluidic shifts could possibly further cause ophthalmic changes including globe flattening, optic disc edema, and optic nerve protrusion, known as microgravity ocular syndromes (MOS). To prevent or reduce the risks of such spaceflight-associated medical conditions, it is critical to understand the effect of microgravity on lymphatic flow and the involvement of such an effect in MOS. To this end, medical imaging techniques serve as important tools to visualize the lymphatic system and measure lymphatic flows. Because lymphatic vessels contain no visible cells and carry mainly clear lymph, they are usually much more difficult to image than blood vessels.

Most medical imaging techniques, including conventional lymphography, computed tomography lymphography, lymphoscintigraphy, and positron emission tomography, need exogenous contrast agents to help visualize lymphatic vessels. However, injection of contrast agents is not suitable for use in spaceflight. Although magnetic resonance lymphography can achieve imaging of the lymphatic system without contrast agents, it is usually too bulky for spaceflight and slow as well.

Ultrasound imaging techniques have been used in spaceships and the International Space Station (ISS). Particularly, ocular ultrasound is used to identify ophthalmic changes involved in MOS. However, to directly visualize the lymphatic system, microbubbles need to be injected to enhance contrast in ultrasound images. Furthermore, ultrasound imaging has limited sensitivity in measuring slow flows such as lymphatic flows in the low-pressure network.

Optical imaging techniques such as near-infrared fluorescence imaging have also been adopted for lymphography. They require injection of fluorescent tracers and suffer from a shallow penetration for high-resolution imaging. Thus, existing imaging techniques, especially when performing lymphography, are fundamentally limited by their need for contrasted agents and/or poor sensitivity in measuring slow flows such as lymphatic flows in the low-pressure lymphatic network.

SUMMARY

Certain aspects pertain to methods and systems for photoacoustic flowgraphy with velocity-matched ultrasonic tagging that can be used, for example, in contrast agent-free lymphatic flowgraphy.

Certain aspects pertain to a method of determining a velocity of flowing material in a vessel using a photoacoustic imaging system. In one implementation, the method includes emitting ultrasonic signals with an ultrasonic transmitter into a moving tagging spot, where the moving tagging spot translates along a segment of the vessel at a plurality of tagging spot velocities; emitting laser pulses with a laser into a reference spot within the segment of the vessel to stimulate a photoacoustic response; receiving, with an ultrasonic receiver, photoacoustic signals generated by the flowing material in response to the laser pulses; identifying, from amongst the received photoacoustic signals, a maximum photoacoustic signal; and determining the velocity of the flowing material by determining which tagging spot velocity resulted in the maximum photoacoustic signal.

Certain aspects pertain to a method of determining a velocity of flowing material in a vessel using a photoacoustic imaging system. In one implementation, the method includes emitting, with an ultrasonic transmitter and a laser, a plurality of sets of ultrasonic signals and laser pulses that translate along the segment of the vessel, such that each set of ultrasonic signals and laser pulses translates along the segment of the vessel at a different speed; receiving, with an ultrasonic receiver, a plurality of sets of photoacoustic signals generated by the flowing material within the vessel in response to the laser pulses, where each set of photoacoustic signals is associated with a respective set of ultrasonic signals and laser pulses; determining that a given set of photoacoustic signals has a peak photoacoustic amplitude greater than any other set of photoacoustic signals, where the given set of photoacoustic signals is associated with a given set of ultrasonic signals and laser pulses that translated along the segment of the vessel at a given speed; and determining the velocity of the flowing material in the vessel based on the given speed of the given set of ultrasonic signals and laser pulses.

These and other features are described in more detail below with reference to the associated drawings.

BRIEF DESCRIPTION OF THE DRAWINGS

FIG. 4A is a schematic diagram of a transducer and carbon fiber showing elevation movement of the transducer, according to an aspect.

FIG. 4B is an axial cross-line profile of the carbon fiber at different elevational locations, according to an aspect.

Figure 1:
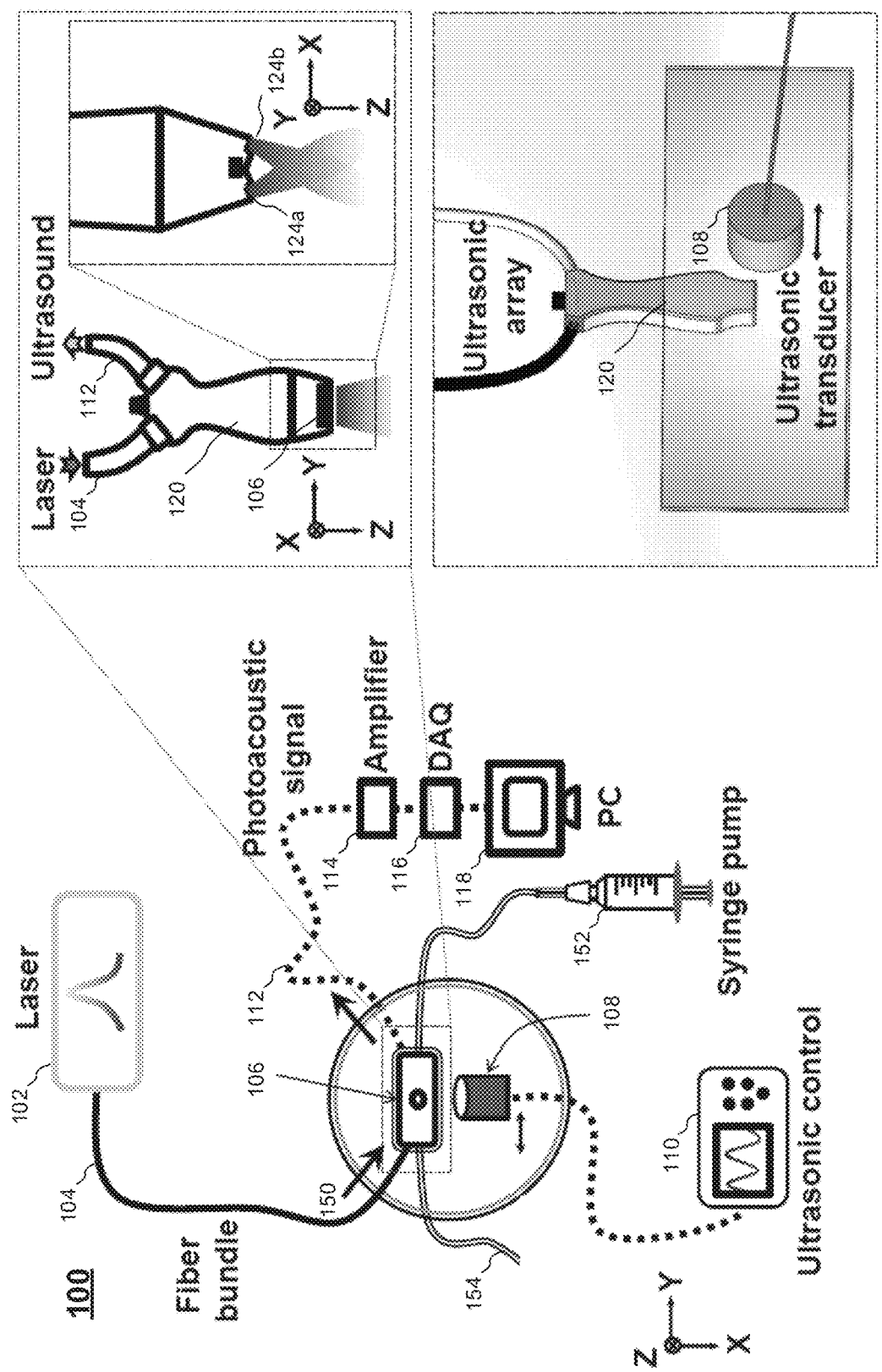
FIG. 1 is a schematic diagram of components of a photoacoustic flowgraphy system with velocity-matched ultrasonic tagging, according to certain implementations.

These and other features are described in more detail below with reference to the associated drawings.

DETAILED DESCRIPTION

Different aspects are described below with reference to the accompanying drawings. The features illustrated in the drawings may not be to scale. In the following description, numerous specific details are set forth in order to provide a thorough understanding of the presented embodiments. The disclosed embodiments may be practiced without one or more of these specific details. In other instances, well-known operations have not been described in detail to avoid unnecessarily obscuring the disclosed embodiments. While the disclosed embodiments will be described in conjunction with the specific embodiments, it will be understood that it is not intended to limit the disclosed embodiments. Certain aspects pertain to velocity-matched ultrasonic tagging in photoacoustic flowgraphy, which can be used, for example, to measure lymphatic fluid flow without the use of exogenous contrast agents.

I. Introduction

The present disclosure sets forth a system that exploits the photoacoustic effect with velocity-matched ultrasonic tagging to perform photoacoustic flowgraphy. In some aspects, the system may be configured for lymphatic flowgraphy (e.g., imaging lymphatic vessels and/or fluid). The disclosed system can image flow of clear liquid in deep tissue without using any exogenous contrast agents, which allows label-free lymphatic imaging.

In general, fluidic flow in the lymphatic vessels (or other structures being imaged) can induce thermal convection and thus reduce the efficiency of ultrasonic tagging. By velocity-matching the ultrasonic tagging to the fluid flow, the sensitivity of the flowgraphy is enhanced. A tagging ultrasonic transducer, driven by a specially designed radio frequency signal, can mechanically scanned along the lymph vessel over a sufficiently wide range of speeds. In some embodiments, a tagging ultrasonic transducer may include an array of ultrasonic transducers configured to emit a steerable ultrasonic beam and the ultrasonic beam can be steered such that a focal point within the lymph vessel scans along the lymph vessel over a sufficiently wide range of speeds. The speeds can cover the empirical range of the fluidic flow speed in lymphatic vessels, typically, 0-10 mm/s. After scanning, the optimal scan speed can be determined from an initial set of photoacoustic signals. In other words, the fluidic flow speed can be determined by identifying which ultrasonic scanning speed resulted in the sharpest (e.g., most focused) ultrasonic tagging. The disclosed system can perform photoacoustic spectroscopy, typically from ~700 to 1,000 nm, and can provide high spatial resolutions in three dimensions. In some configurations, the system can provide spatial resolutions of 85 µm, 260 µm and 650 µm in the axial, lateral and elevational directions, respectively.

II. Velocity-Matched Ultrasonically-Tagged Photoacoustic Lymphatic Flowgraphy (VMUT-PALF)

FIG. 1 is a schematic diagram of components of a photoacoustic flowgraphy system 100 with velocity-matched ultrasonic tagging, according to certain implementations. Such a system may also be referred to herein as velocity-matching ultrasonically tagged photoacoustic lymphatic flowgraphy (VMUT-PALF). Although the present disclosure describes the system primarily in connection with lymphatic flowgraphy (e.g., the imaging of lymphatic vessels and lymphatic fluid), the disclosed system can be used for imaging (e.g., flowgraphy) of other structures or objects, whether anatomical, mechanical, or otherwise. Additionally, while the present disclosure references applications for medical imaging in spaceflight, the disclosed system can be used in biomedicine and other application on Earth.

The photoacoustic flowgraphy system 100 of FIG. 1 includes, as examples, a laser source 102, fiber bundle 104, ultrasonic receiver 106, an ultrasonic transmitter 108, ultrasonic controller 110, ultrasound signal cable 112, amplifier 114, data acquisition unit (DAQ) 116, and computing resources 118 (e.g., a PC, computer, service, or other device having computing capabilities). As shown in the breakout of FIG. 1, system 100 may also include a combined ultrasound-laser head 120 having an ultrasound receiver 106 and one or more fiber ends such as fiber ends 124a and 124b.

Laser source 102 may be configured to generate photoacoustic signals in a subject such as subject 150. In the example of FIG. 1, subject 150 is a simulated lymphatic vessel formed from human tissue-mimicking materials (e.g., silicon tubes immersed in agar and 2% intralipid). Pump 152 was utilized to push the simulated fluid through the subject vessel 154 (e.g., flow tube 154) at controllable and adjustable velocities. In practice, system 100 can be used to image human subjects as well as other biological and non-biological vessels where sensitive flowgraphy without the requirement of contrast agents is desired. If desired, however, system 100 can image subjects to which one or more contrast agents have been added or injected.

Laser source 102 may include, as an example, an optical parametric oscillator (OPO) pumped by a Nd:YAG (neodymium-doped yttrium aluminium garnet) laser. In some configurations, laser source 102 is configured to provide laser pulses having a pulse width of approximately 10 nanoseconds (ns) and a pulse repetition rate of approximately 50 Hz. The laser source 102 can be spectrally tuned. In some embodiments, the laser source 102 can be spectrally tuned to a plurality of frequencies as a part of performing photoacoustic spectroscopy (e.g., imaging a subject using the photoacoustic effect with a variety of frequencies of photoacoustic stimulating laser pulses). As specific examples, the laser source 102 can be spectrally tuned to wavelengths of 680 to 980 nm. The laser source 102 may also provide a controllable or configurable pulse energy over the tuning range. As an example, laser source 102 may be configure to provide sufficient pulse energy that the photoacoustic signal has an acceptable signal-to-noise ratio, while also ensuring that the laser fluence remains below health and safety limits. As a specific example, the laser source 102 may be configured to provide a pulse energy of approximately 200 mJ over the tuning range. To ensure and improve safety, the laser beam emitted by laser source 102 may be concealed and delivered to the subject (e.g., a person's skin, an object being imaged, etc.) though an optical fiber bundle such as fiber bundle 104. In some configurations, the laser fluence on the subject is less than 20 mJ/cm2, well below the ANSI laser safety limit for human exposure (e.g., the ANSI safety limit may be a maximum permissible exposure of 69 mJ/cm$^2$ at 970 nm, a water-absorption wavelength).

Ultrasonic receiver 106 may be formed from an array of ultrasonic receivers or transducers. The ultrasonic receiver 106 may have a working frequency range of approximately 13 MHz to approximately 24 MHz and may be configured to detect laser-generated photoacoustic signals (e.g., acoustic signals generated by subject 150 upon stimulation with laser pulse(s) from laser source 102. The ultrasonic receiver 106 may be combined with the emitting ends 124a and/or 1224b of optical fibers 104 in a common ultrasound-laser head 120. The photoacoustic signals received by ultrasonic receiver 106 may be routed over cable 112, amplified by amplifier 114, and received by data acquisition ultrasound-laser (DAQ) unit 116. DAQ 116, together with computing resources 118, includes signal processing capabilities and are configured to reconstruction photoacoustic images and measurements based on the received photoacoustic signals.

As part of quantifying flow without the use of exogenous contrast agents, ultrasound emitter 108 is used to ultrasonically tag the subject 150. Ultrasound emitter 108 may be formed from an array of ultrasonic emitters or transducers. Ultrasound emitter 108 may, in some configurations, be operated at 3.3 MHz, although other frequencies can also be utilized. In general, the frequency of ultrasound emitter 108 can be varied to optimize (e.g., increase) the efficacy of the ultrasonic tagging, or for other purposes.

The ultrasonic tagging signals provided by ultrasonic emitter 108 may be translated along the axial direction of the subject being imaged (e.g., simulated subject 150, a lymphatic vessel, or another subject being imaged). In some embodiments, it may be desirable to translate the ultrasonic tagging signals at a speed that matches, or nearly matches, the speed of fluid flow within the subject being imaged. With such an arrangement, the ultrasonic tagging signals are focused upon (e.g., traveling with) a particular volume of moving fluid, as opposed to a particular location within the vessel. As a result, the ultrasonic tagging signals produce a sharper heating within the vessel, by heating a particular volume of moving fluid, as opposed to heating all the fluid that passes through a particular location. In other words, the efficacy of the ultrasonic tagging is improved or maximized.

Translation of the ultrasonic tagging signals may be accomplished by mechanically scanning the ultrasonic emitter 108 (as shown in FIG. 1) along the direction of fluid flow in the subject being imaged. In other embodiments, translation of the ultrasonic tagging signals may be accomplished by mechanically rotating the ultrasonic emitter 108. If desired, the focus point of the ultrasonic emitter 108 may be varied during the rotation in order to provide focused ultrasonic tagging signals that translate along the subject being imaged at controllable rates. In still other embodiments, the ultrasonic emitter 108 may be formed of an electronically steerable phased array of ultrasound emitters. In such embodiments, the phased array may be electronically steered (e.g., by altering the phase delays between the elements of the phased array) such that the focal point of the tagging ultrasound signals traverses the subject being imaged at controllable rates.

If desired, the ultrasonic emitter 108 may be combined with the ultrasonic receiver 106. As a first example, ultrasonic receiver 106 and ultrasonic emitter 108 may be separate elements in a combined ultrasonic head (which may also include laser emitting elements such as optical fiber ends 124a and/or 124b). As a second example, a single ultrasonic transducer (which may be an array of transducer elements) can implement the functionality of both ultrasonic receiver 106 and ultrasonic emitter 108.

Due to the ultrasonic absorption by the fluid or tissue (e.g., of the tagging signals from emitter 108), the temperature of the subject being imaged increases at the ultrasonically tagged volume. Correspondingly, this local temperature increase produces a photoacoustic signal change (e.g., a change in the ultrasonic signals received by receiver 106 following stimulation by laser light from laser source 102), which is given by:

$$p_0(t,x) = [a + bT_0 + b\tilde{T}(t,x)]\mu_a(x)F(x), \quad (1)$$

where $p_0$ denotes the initial photoacoustic pressure, t denotes time, x denotes displacement along the lymph vessel, a and b denote constants, $T_0$ denotes the baseline temperature, $\tilde{T}(t,x)$ denotes the temperature change due to the ultrasonic tagging, $\mu_a(x)$ denotes the optical absorption coefficient, and $F(x)$ denotes the laser fluence used for generating the photoacoustic signal.

Figure 2:
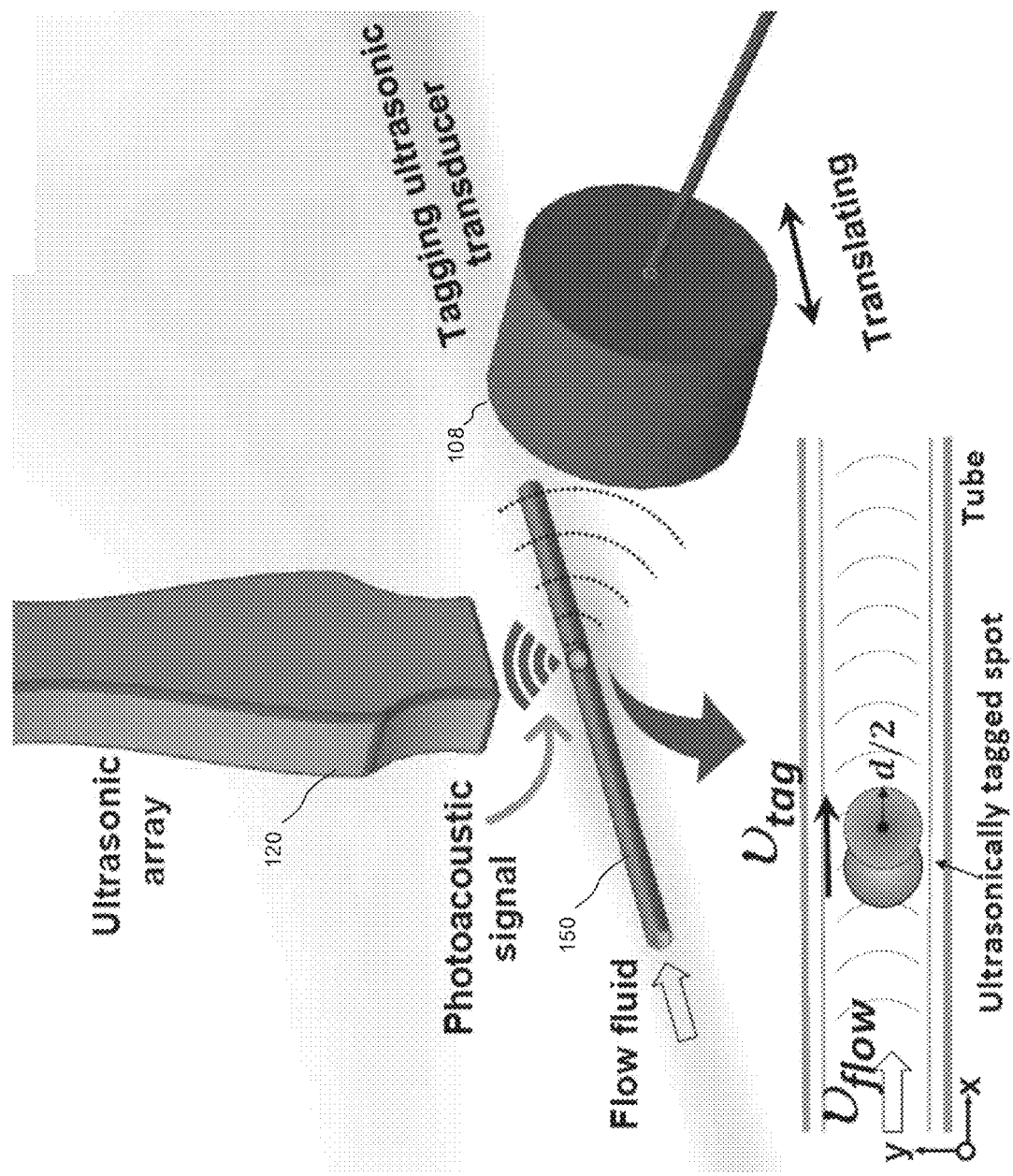
FIG. 2 schematically illustrates translating an ultrasonic transducer as part of photoacoustic flowgraphy system with velocity-matched ultrasonic tagging, according to an aspect.

For a fluidic flow that has a flow speed of $v_{flow}$, as shown in FIG. 2, the temperature rise generated by the tagging ultrasonic transducer translating at a speed of $v_{tag}$ is:

$$\tilde{T}(t, x) = \frac{Q(v_{flow}, v_{tag})}{mC}, \quad (2)$$

where Q is the heat accumulated from the tagging ultrasound, m is the mass of the ultrasonically tagged volume, and C is the specific heat capacity.

To simplify, consider a 1D case, as shown in FIG. 2, where the ultrasonic axis is perpendicular to the flow direction, x-axis. The pressure amplitude distribution of the tagging ultrasound spot along the x-axis is denoted by $p(x-x_0)$, where $x_0$ is the tagging position at t=0. When the tagging ultrasonic transducer is translated at velocity $v_{tag}$, the time-dependent envelope becomes $p(x-x_0-v_{tag}t)$.

For a tagging duration of $T_{tag}$, the effective envelope of the tagging ultrasound from t=0 can be expressed as $\theta(t)\theta(T_{tag}-t)p(x-x_0-v_{tag}t)$, where $\theta(t)$ is a step function. If the fluid flows along x at velocity $v_{flow}$, for a fluidic spot originally located at $x_p$ with a size of $\Delta x$, the heat accumulation is given by:

$$Q = \int_0^{T_{tag}} dt \int_{x_p+v_{flow}t}^{x_p+v_{flow}t+\Delta x} p(x-x_0-v_{tag}t)dx. \quad (3)$$

When $\Delta x$ is small, Eq. 3 can be simplified to:

$$Q = \int_0^{T_{tag}} dt \, p(x_p,x_0+(v_{flow}-v_{tag})t) \quad (4)$$

Obviously, Q reaches the maximum when $v_{flow}=v_{tag}$ and $x_p=x_0$. At the maximum, the highest fractional photoacoustic signal is produced, correspondingly the maximum sensitivity of the VMUT-PALF imaging system 100 is reached.

III. Resolution of the VMUT-PALF System

The spatial resolutions (e.g., axial, elevational, and lateral) of the VMUT-PALF imaging system 100 were quantified using a micro carbon fiber 300. Carbon fiber 300 had a diameter of 30 μm.

Figure 3A:
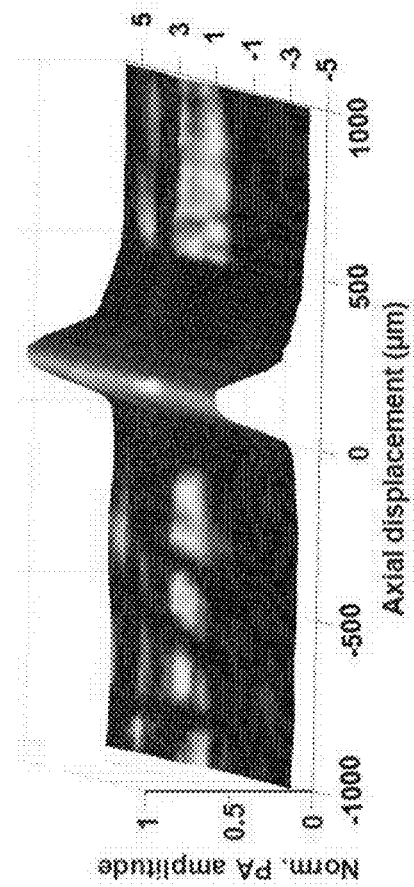
FIG. 3A is a schematic diagram of a transducer and carbon fiber showing axial movement of the transducer, according to an aspect.
Figure 3B:
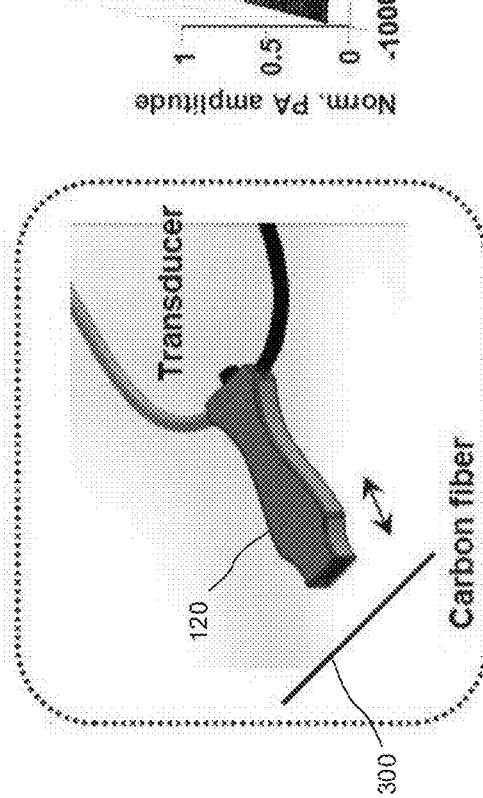
FIG. 3B is an axial cross-line profile of the carbon fiber at different axial depths, according to an aspect.
Figure 3C:
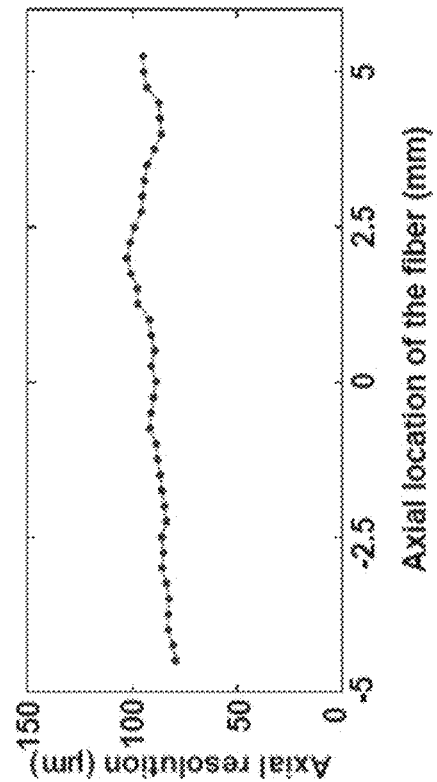
FIG. 3C is a graph of the axial point spread function, according to an aspect.
Figure 3D:
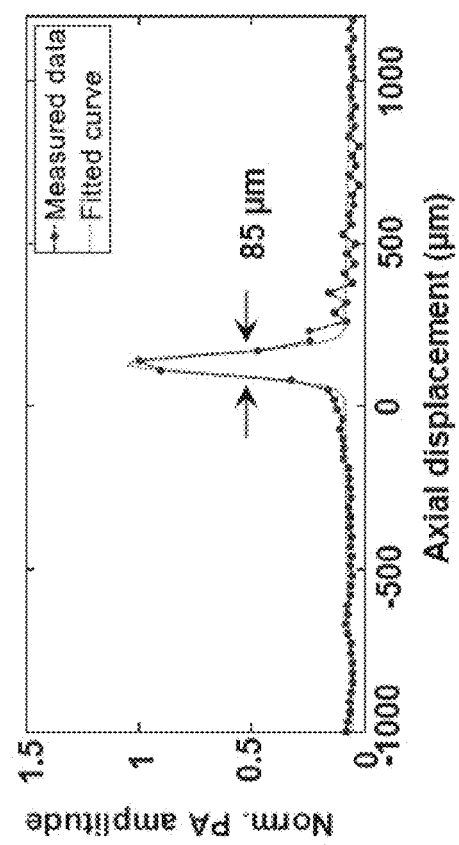
FIG. 3D shows the axial resolution over an axial depth range, according to an aspect.

To determine the axial resolution, carbon fiber 300 was scanned in the axial direction on the elevational focal plane. In particular, carbon fiber 300 was translated towards and away from the combined ultrasound-laser head 120 as shown in FIG. 3A. An axial cross-line profile of the micro carbon fiber 300 at different axial depths is shown in FIG. 3B. A point spread function in the axial direction (at 0 mm) is shown in FIG. 3C. The axial resolution (full width at half maximum) over an axial depth range of 10 mm is shown in FIG. 3D. Based on the results of scanning carbon fiber 300 in the axial direction, the axial resolution of the VMUT-PALF imaging system 100 was determined to be approximately 85 μm over a 10-mm axial range (extending plus or minus 5 mm from the axial focus), as shown in FIG. 3D.

Figure 4C:
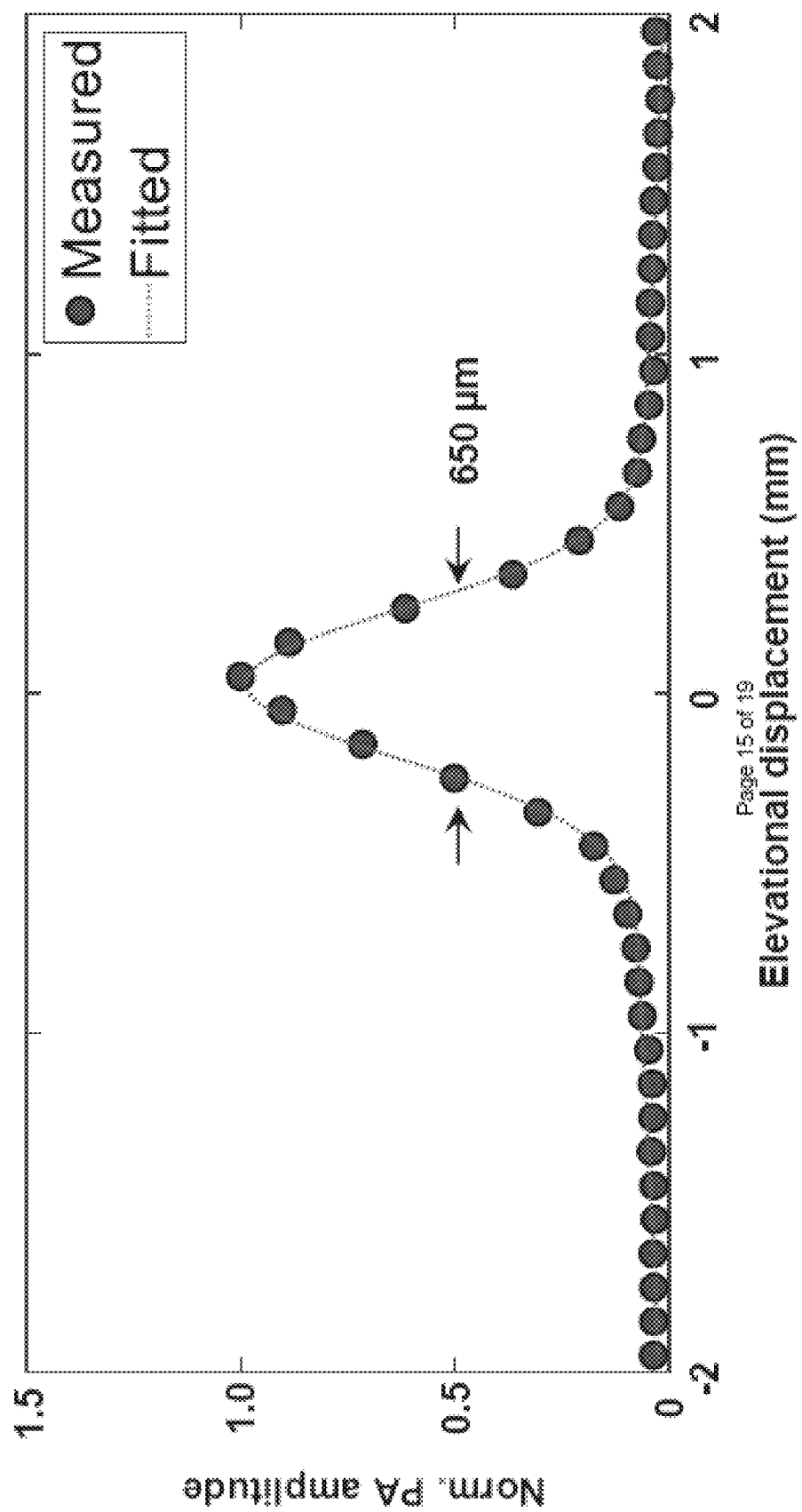
FIG. 4C is a graph of the elevational point spread function, according to an aspect.

To determine the elevational resolution, the carbon fiber 300 was scanned in the elevation direction as illustrated in FIG. 4A. An axial cross-line profile of the carbon fiber 300 at different elevational locations is shown in FIG. 4B. An elevational point spread function along the dashed line 400 of FIG. 3B is shown in FIG. 4C. Based on the results of scanning carbon fiber 300 in the elevational direction, the elevational resolution of the VMUT-PALF imaging system 100 was determined to be approximately 650 μm, as shown in FIG. 4C.

Figure 5:
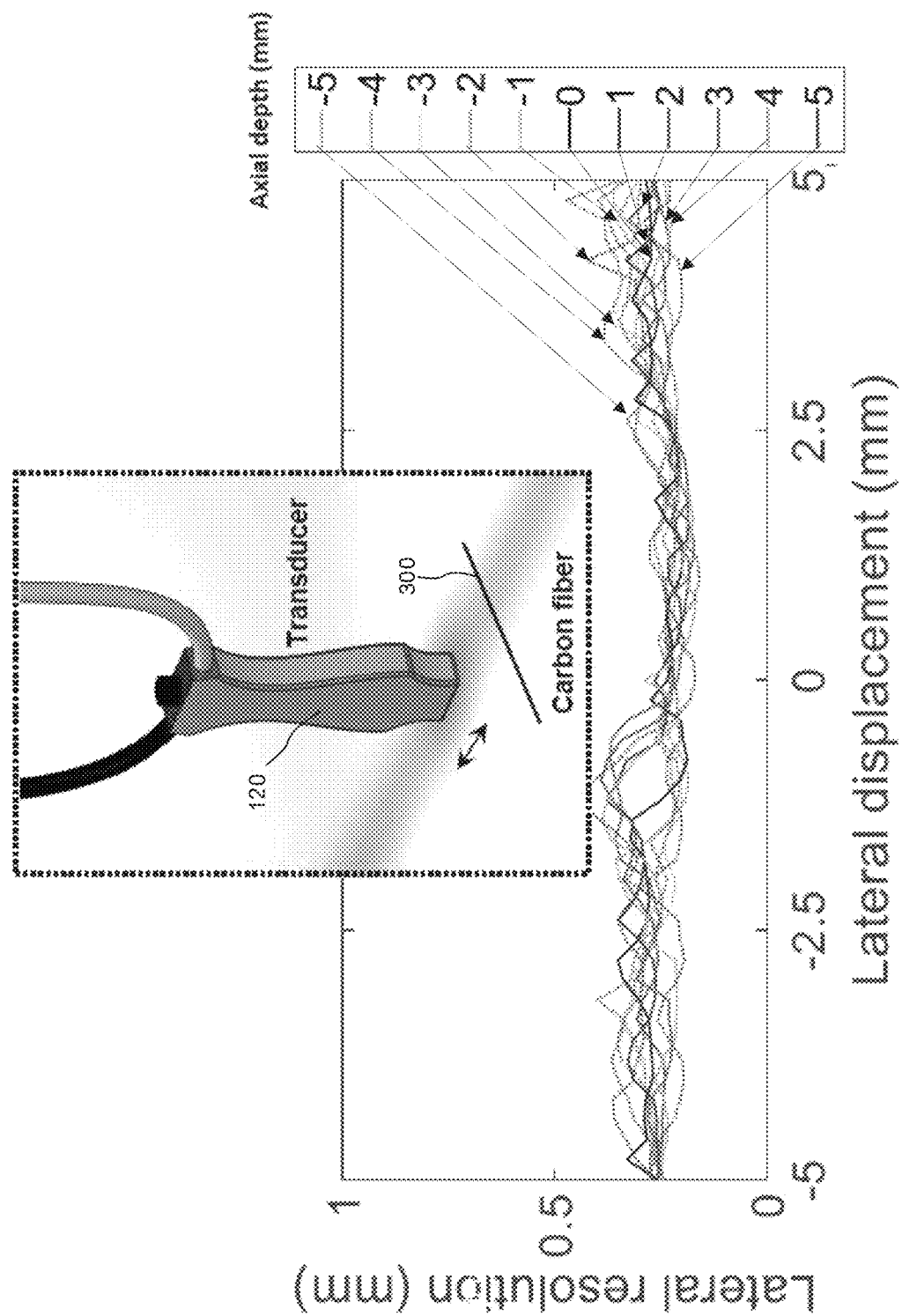
FIG. 5 shows a schematic diagram of a transducer and carbon fiber showing lateral movement of the transducer and a graph of the lateral resolution at various axial depths, according to an aspect.

To determine the lateral resolution, the carbon fiber 300 was scanned in the lateral direction at different axial depths (e.g., −5 mm to +5 mm offset from the axial focus) as illustrated in FIG. 5. Based on the results of scanning carbon fiber 300 in the lateral direction, the lateral resolution of the VMUT-PALF imaging system 100 was determined to be approximately 260 μm.

IV. Measuring Fluidic Flow Speed with the VMUT-PALF System

To validate the VMUT-PALF imaging system 300 for flow measurement, a tissue-mimicking phantom was used as a test subject 150. In particular, the test subject 150 was formed from silicone tubes immerges in agar and 2% intralipid with a fluid pumped through the tubes as a controlled and steady rate. The tagging ultrasonic emitter 108 was driven with a radiofrequency (RF) signal illustrated in element (a) of FIG. 6. The duty cycle of the RF signal (e.g., the ultrasonic tagging signal) was preliminarily set to 20%, e.g., ultrasonic tagging for 1 second, idling for 4 seconds, and then repeating. In practice, the duty cycle of the ultrasonic tagging could be set to any desirable level. During the ultrasonic tagging (e.g., the 20% "on" portion of the duty cycle), a 3.3 MHz sinusoidal waveform modulated by a 90%-duty-cycle square wave at 50 HZ is applied to the tagging ultrasonic emitter 108. This particular RF signal was chosen to avoid RF amplification saturation in the signal processing unit, although it should be noted that other RF signals may also be utilized.

Figure 6:
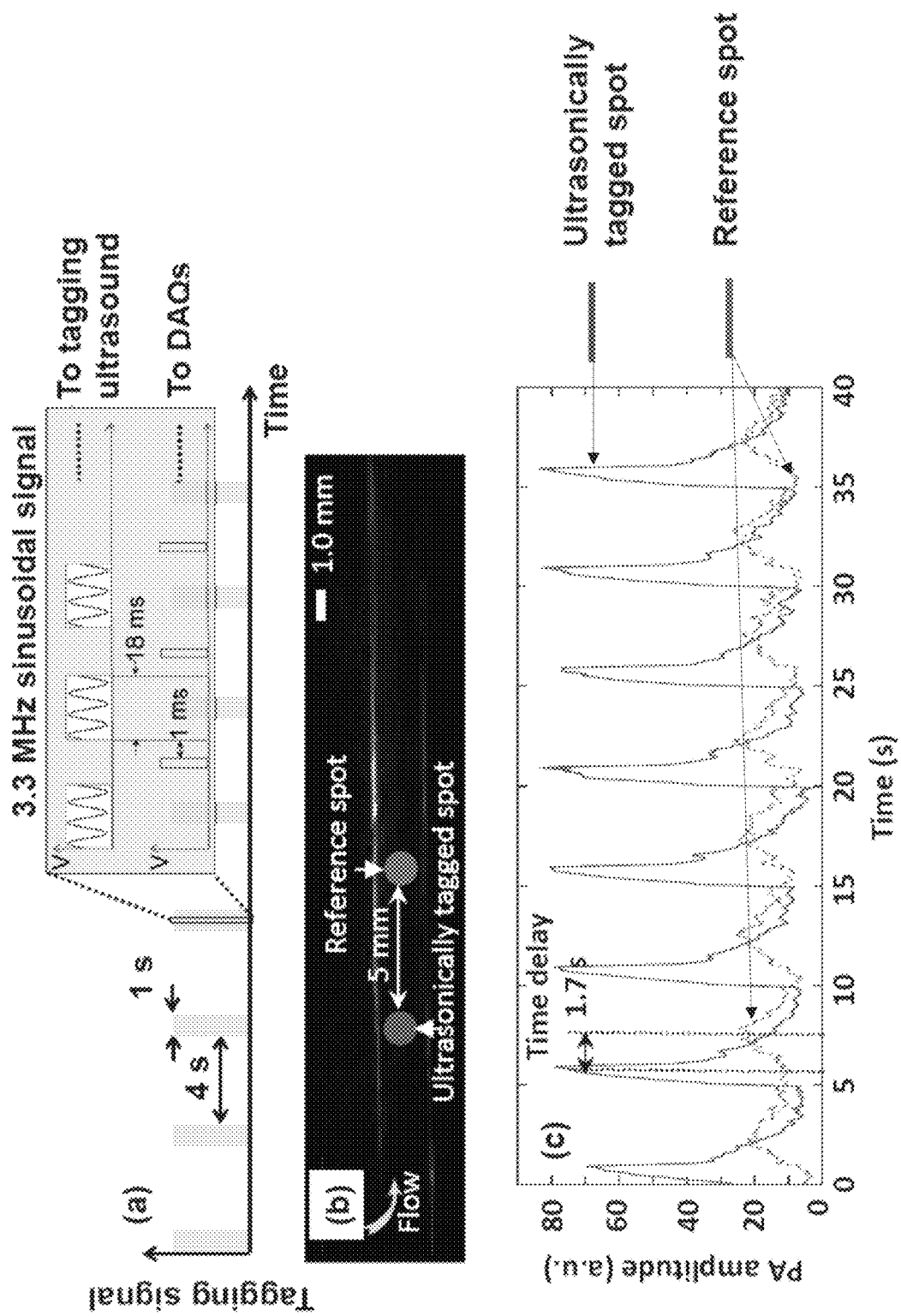
FIG. 6 shows (a) a signal sequence, (b) a photoacoustic image of a silicone tube with fluidic flow, and (c) photoacoustic signals at two locations within the tube, according to an aspect.
Figure 7:
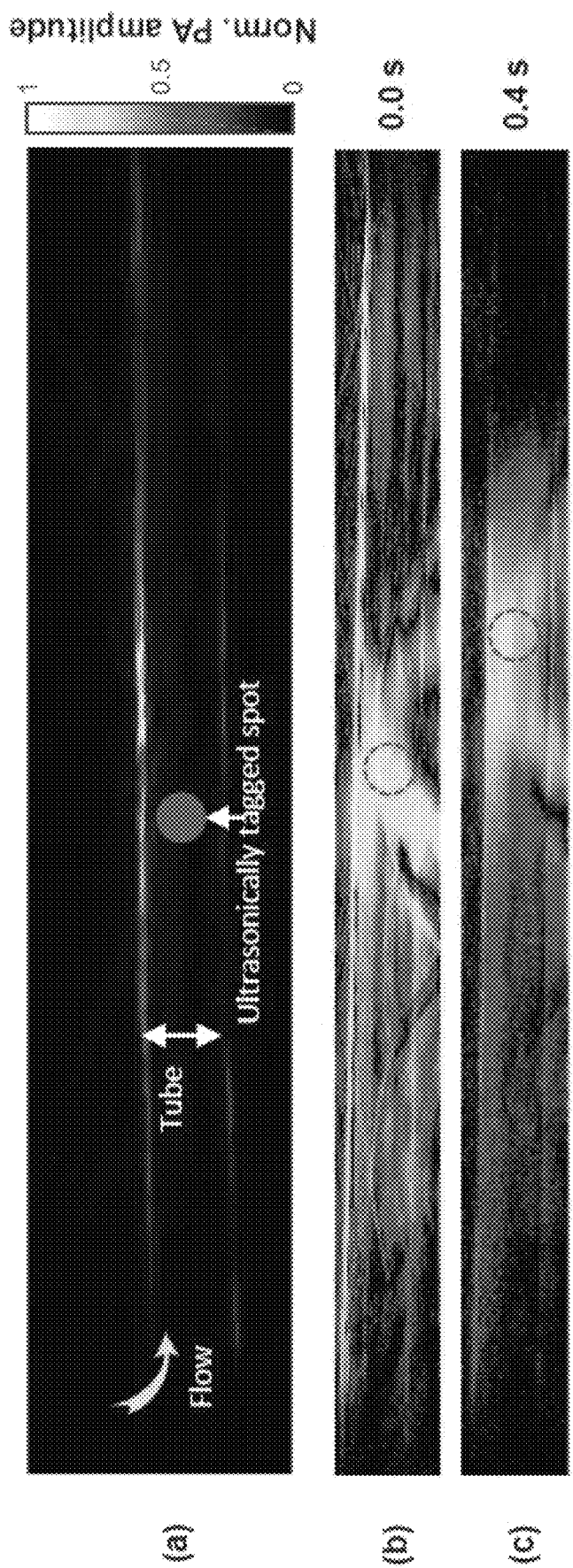
FIG. 7 shows (a) a photoacoustic image of a silicone tube with fluidic flow and (b) consecutive images of an ultrasonically tagged spot at different times, according to an aspect.

As shown in element (b) of FIG. 6, photoacoustic signals were obtained (e.g., by providing laser pulses using laser 102 and receiving the photoacoustic responses using receiver 106) from the ultrasonically tagged spot and a reference spot 5 mm downstream. The resulting photoacoustic signals are plotted in element (c) of FIG. 6. As shown in FIG. 6, the photoacoustic signal changes (resulting from the ultrasonic tagging) have a time delay that is determined by the fluidic flow speed. The movement of the ultrasonically tagged spot is visualized in the consecutive frames of elements (b) and (c) of FIG. 7, where the two frames are separated by 0.4 seconds. In the example of FIG. 6, the fluidic flow speed was set to approximately 3.0 mm/s and the measured time delay was approximately 1.7 seconds, which is as expected given the 5 mm separation between the reference spot and the ultrasonically tagged spot. If desired, this time delay may itself be used in measuring fluid flow. In particular, the VMUT-PALF system 100 may ultrasonically tag a first location within a fluid-carrying vessel, monitor a second location within the vessel downstream of the first, and then calculate the fluid velocity by dividing the distance between the first and second locations by the measured time delay (e.g., how long it takes for the effects of the tagging signal to travel to the second location). The positions of the first and second locations, and the distance therebetween, may be determinable based on properties of the system such as the focal points of the ultrasonic tagger and the laser source.

In some embodiments, the VMUT-PALF system 100 may be able to measure fluidic flow speed by monitoring at least one spot downstream of the ultrasonically tagged spot within a vessel, as discussed above in connection with FIGS. 6 and 7. The photoacoustic signal from the ultrasonically tagged spot is not required (although it may be beneficial), as the time(s) at which the ultrasonically tagged spot is heated is (are) known. With arrangements of this type, the distance between the ultrasonically tagged spot and at least one downstream and photoacoustically-monitored spot can be determined by the known properties of the VMUT-PALF system 100 (e.g., the positions and angles of the various receivers and emitters, their focal positions, etc.). Additionally, the time it takes fluid to flow from the ultrasonically tagged spot to the reference spot can be determined by determining the time delay between the ultrasonic tagging and a jump in photoacoustic response at the reference spot (or between a jump in photoacoustic response at a first reference spot which may be the tagged spot and a corresponding jump in photoacoustic response at a second reference spot downstream of the first).

In other embodiments, the VMUT-PALF system 100 may be able to measure fluidic flow speed by velocity-matching the ultrasonic tagging to the fluidic flow. In general, the fluidic flow, including lymphatic flow in lymphatic vessels, induces thermal convention within the fluid, spreading out the thermal energy of an ultrasonic tagging and reducing the efficiency of the ultrasonic tagging. As previously described, the ultrasonic tagging signals provided by ultrasonic emitter 108 may be translated along the axial direction of the subject being imaged (e.g., by mechanical and/or electronic means). While the discussion below describes mechanically translating the emitter 108, it should be understood that other techniques may be similarly employed (e.g., rotating the emitter 108, electronically steering a phased array emitter, etc.).

Figure 8:
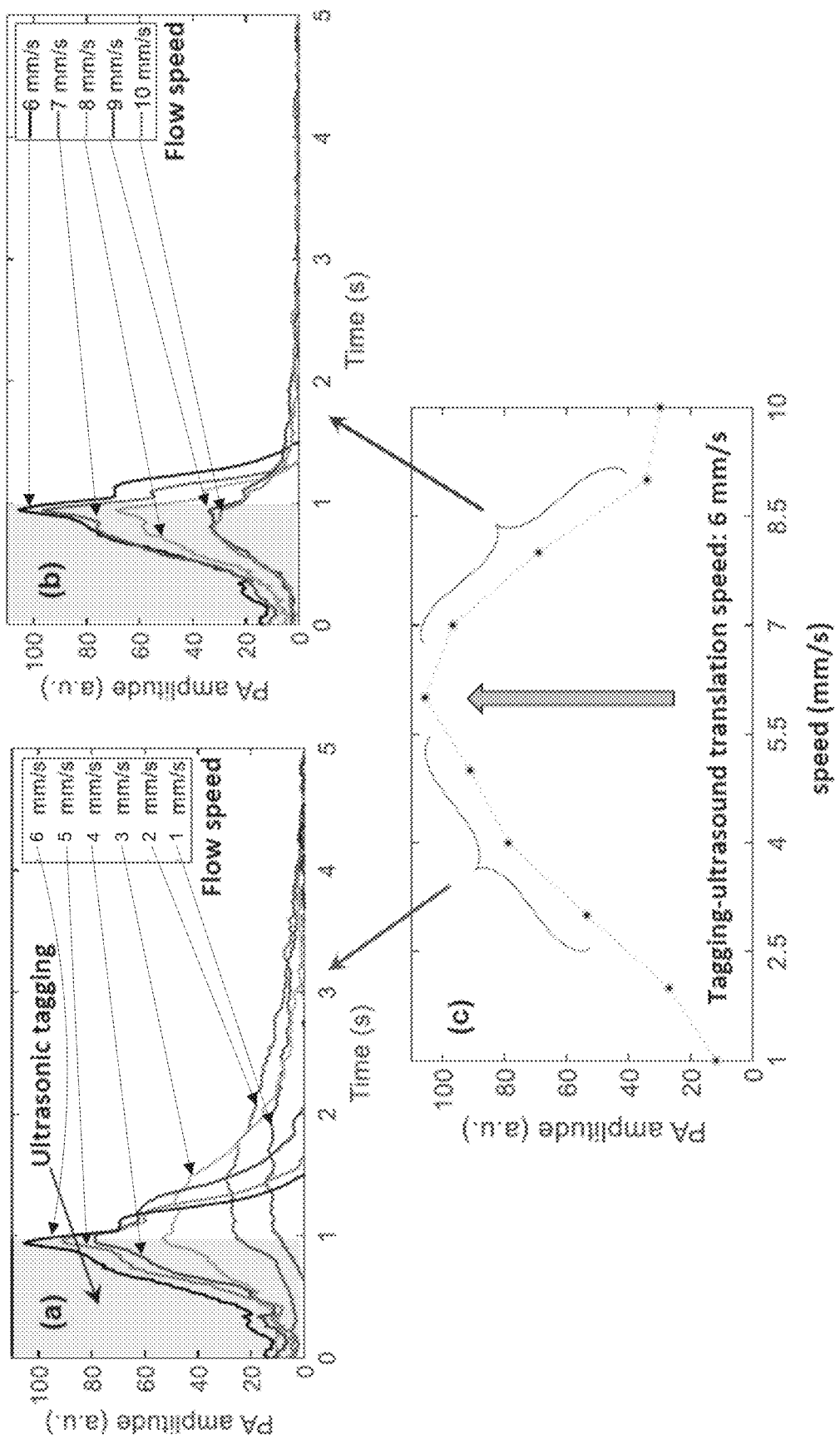
FIG. 8 shows (a, b) photoacoustic signals at various flow speeds with a fixed ultrasonic tagging speed and (c) peak photoacoustic amplitudes for the various flow speeds, according to an aspect.

An example of fluidic flow speed measurement by velocity-matching the ultrasonic tagging to the fluidic flow using the VMUT-PALF system 100 is shown in FIG. 8. In the example of FIG. 8, the tagging ultrasonic emitter 108 was translated along the direction of the fluidic flow over a range of speeds. The range of speeds was selected to cover the empirical range of fluidic flow speed in lymphatic vessels, e.g., 0-10 mm/s. In general, when measuring fluidic flow speed with system 100, it may be desirable to translate the tagging ultrasonic emitter 108 across the potential or expected ranges of speeds of the subject being imaged. In some embodiments, a hunting algorithm may be used to select different translation velocities to more quickly find the speed of the fluidic flow. As an example of a hunting algorithm for lymphatic flow, the system could be translated at a variety of speeds that are relatively widely separated (e.g., 0, 3, 6, and 9 mm/s), a maximum photoacoustic signal amongst the tested speeds determined, and then at least one additional round of testing performed around the velocity having the maximum photoacoustic signal (e.g., if the 6 mm/s test had the largest signal, the next round might test 4, 5, 6, 7, and 8 mm/s). Additional rounds can be performed until the speed of the fluidic flow is determined to the desired accuracy or the accuracy limit of the system. If desired, other algorithms for selecting test velocities may be utilized.

When the translation speed of the tagging ultrasonic emitter 108 matches the velocity of the fluidic flow, the efficiency of the tagging ultrasonic emitter 108 may be maximized. The VMUT-PALF system 100 may detect this condition by identifying the corresponding maximum in the photoacoustic return signals. In the FIG. 8 example, the photoacoustic responses are plotted in element (a) for tagging translations speeds of 1 mm/s to 6 mm/s and in element (b) for speeds of 6 mm/s to 10 mm/s (in 1/mm/s increments). The ultrasonic tagging was applied for one second, while the photoacoustic stimulation and monitoring continued a few seconds thereafter. The photoacoustic results shown in elements (a) and (b) show a clear lock-in effect, where the amplitude of the photoacoustic signal is greatly increased the closer the translation speed is to the actual fluidic flow velocity. Thus, by varying the translation speed and finding the resulting maximum in the photoacoustic respond, it is possible to measure the velocity of the fluidic flow. The peak photoacoustic amplitude as a function of the translation speed of the tagging ultrasonic emitter 108 is graphed in element (c) of FIG. 8. As illustrated, the peak photoacoustic signal resulted from a translation speed of 6 mm/s, which can be taken as the system's measurement of the velocity of the fluidic flow.

While much of the present disclosure refers to flowgraphy of lymphatic fluid, the VMUT-PALF system 100 can be utilized for other applications (e.g., imaging other biological vessels or tubes, imaging non-biological fluid flow, imaging biological or non-biological fluid flow outside of a vessel or tube, etc.).

V. Additional Considerations

Modifications, additions, or omissions may be made to any of the above-described embodiments without departing from the scope of the disclosure. Any of the embodiments described above may include more, fewer, or other features without departing from the scope of the disclosure. Additionally, the steps of described features may be performed in any suitable order without departing from the scope of the disclosure. Also, one or more features from any embodiment may be combined with one or more features of any other embodiment without departing from the scope of the disclosure. The components of any embodiment may be integrated or separated according to particular needs without departing from the scope of the disclosure. For example, it would understood that while certain PACT systems are described herein with a linear stage, another mechanism may be used.

It should be understood that certain aspects described above can be implemented in the form of logic using computer software in a modular or integrated manner Based on the disclosure and teachings provided herein, a person of ordinary skill in the art will know and appreciate other ways and/or methods to implement the present invention using hardware and a combination of hardware and software.

Any of the software components or functions described in this application, may be implemented as software code using any suitable computer language and/or computational software such as, for example, Java, C, C#, C++ or Python, LabVIEW, Mathematica, or other suitable language/computational software, including low level code, including code written for field programmable gate arrays, for example in VHDL. The code may include software libraries for functions like data acquisition and control, motion control, image acquisition and display, etc. Some or all of the code may also run on a personal computer, single board computer, embedded controller, microcontroller, digital signal processor, field programmable gate array and/or any combination thereof or any similar computation device and/or logic device(s). The software code may be stored as a series of instructions, or commands on a CRM such as a random access memory (RAM), a read only memory (ROM), a magnetic medium such as a hard-drive or a floppy disk, or an optical medium such as a CD-ROM, or solid stage storage such as a solid state hard drive or removable flash memory device or any suitable storage device. Any such CRM may reside on or within a single computational apparatus, and may be present on or within different computational apparatuses within a system or network. Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

What is claimed is:

1. A method of determining a velocity of flowing material in a vessel using a photoacoustic imaging system, the method comprising:
with an ultrasonic transmitter, emitting ultrasonic signals into a moving tagging spot, wherein the moving tagging spot translates along a segment of the vessel at a plurality of tagging spot velocities;
with a laser, emitting laser pulses into a reference spot within the segment of the vessel to stimulate a photoacoustic response;
with an ultrasonic receiver, receiving photoacoustic signals generated by the flowing material in response to the laser pulses;
identifying, from amongst the received photoacoustic signals, a maximum photoacoustic signal; and
determining the velocity of the flowing material by determining which tagging spot velocity resulted in the maximum photoacoustic signal.

2. The method of claim 1, wherein the flowing material comprises lymphatic fluid and wherein the vessel comprises a lymphatic vessel.

3. The method of claim 1, wherein the plurality of tagging spot velocities comprise a plurality of velocities no greater than 10 mm/s.

4. The method of claim 1, wherein emitting the ultrasonic signals comprises:
with the ultrasonic emitter, emitting first ultrasonic signals into a first moving tagging spot that translates along the segment at a first speed; and
with the ultrasonic emitter, emitting second ultrasonic signals into a second moving tagging spot that translates along the segment at a second speed.

5. The method of claim 1, wherein the reference spot comprises a stationary reference spot located downstream of at least a portion of the moving tagging spot.

6. The method of claim 1, wherein the reference spot comprises a moving reference spot.

7. The method of claim 1, wherein the reference spot comprises a moving reference spot that tracks the moving tagging spot and also translates along the segment of the vessel at the plurality of tagging spot velocities.

8. The method of claim 1, wherein emitting the translating ultrasonic signals and laser pulses comprises emitting the laser pulses through optical fibers that are aligned coaxially with the ultrasonic transmitter.

9. The method of claim 1, wherein emitting the translating ultrasonic signals and laser pulses comprises emitting the laser pulses through optical fibers that are aligned coaxially and confocally with the ultrasonic transmitter.

10. The method of claim 1, wherein emitting the translating ultrasonic signals comprises mechanically translating the ultrasonic transmitter along the segment of the vessel at the plurality of tagging spot velocities.

11. The method of claim 1, wherein emitting the translating ultrasonic signals comprises mechanically rotating the ultrasonic transmitter such that the ultrasonic signals translate along the segment of the vessel at the plurality of tagging spot velocities.

12. The method of claim 1, wherein the ultrasonic transmitter comprises a phased array of ultrasound emitting elements and wherein emitting the translating ultrasonic signals comprises electronically steering a focus spot of the phased array along the segment of the vessel at the plurality of tagging spot velocities.

13. The method of claim 1, wherein emitting the laser pulses comprises emitting translating laser pulses through at least one optical fiber and mechanically translating the optical fiber along the segment of the vessel at the plurality of tagging spot velocities.

14. A method of determining a velocity of flowing material in a vessel using a photoacoustic imaging system, the method comprising:
with an ultrasonic transmitter and a laser, emitting a plurality of sets of ultrasonic signals and laser pulses that translate along the segment of the vessel, such that each set of ultrasonic signals and laser pulses translates along the segment of the vessel at a different speed;
with an ultrasonic receiver, receiving a plurality of sets of photoacoustic signals generated by the flowing material within the vessel in response to the plurality of sets of laser pulses, wherein each set of photoacoustic signals is associated with a respective set of ultrasonic signals and laser pulses;
determining that a given set of photoacoustic signals has a peak photoacoustic amplitude greater than any other set of photoacoustic signals, wherein the given set of photoacoustic signals is associated with a given set of ultrasonic signals and laser pulses that translated along the segment of the vessel at a given speed; and
determining the velocity of the flowing material in the vessel based on the given speed of the given set of ultrasonic signals and laser pulses.

15. The method of claim 14, wherein the flowing material comprises lymphatic fluid and wherein the vessel comprises a lymphatic vessel.

16. The method of claim 14, wherein each set of ultrasonic signals and laser pulses translates along the segment at a respective speed no greater than 10 mm/s.

17. The method of claim 14, wherein emitting the plurality of sets of ultrasonic signals and laser pulses with the ultrasonic transmitter and the laser comprises emitting the plurality of sets of ultrasonic signals and laser pulses with an acoustic-optical head including an ultrasound array and optical fibers that are aligned confocally with the ultrasound array.

18. The method of claim 14, wherein emitting the plurality of sets of ultrasonic signals and laser pulses that translate along the segment of the vessel comprises mechanically translating the ultrasonic transmitter and an optical fiber end coupled to the laser along the segment of the vessel.

19. The method of claim 14, wherein emitting the plurality of sets of ultrasonic signals and laser pulses that translate along the segment of the vessel comprises mechanically rotating the ultrasonic transmitter and an optical fiber end coupled to the laser such that the ultrasonic signals and laser pulses translate along the segment of the vessel.

20. A system for measuring a velocity of flowing material in a vessel, the system comprising:
an ultrasonic transmitter configured to emit ultrasonic signals into a moving tagging spot that translates along a segment of the vessel at a plurality of tagging spot velocities;
a laser source configured to emit laser pulses into a reference spot within the segment of the vessel to stimulate a photoacoustic response by the flowing material;
an ultrasonic receiver configured to receive photoacoustic signals generated by the flowing material in response to the laser pulses; and
computing equipment configured to identify, from amongst the received photoacoustic signals, a maximum photoacoustic signal and to determine the velocity of the flowing material by determining which tagging spot velocity resulted in the maximum photoacoustic signal.

21. The system of claim 20, further comprising one or more optical fibers coupled to the laser source and having optical fiber ends through which the laser pulses are emitted.

22. The system of claim 21, wherein the ultrasonic transmitter and the one or more optical fibers are combined into a single optical-acoustic head.

23. The system of claim 22, wherein the ultrasonic transmitter is aligned coaxially and confocally with the one or more optical fibers.

24. The system of claim 20, wherein the ultrasonic transmitter comprises an electronically-steerable phased array.

* * * * *